United States Patent
Mengüçet al.

(10) Patent No.: US 6,721,051 B2
(45) Date of Patent: Apr. 13, 2004

(54) NON-INTRUSIVE METHOD AND APPARATUS FOR CHARACTERIZING PARTICLES BASED ON SCATTERING MATRIX ELEMENTS MEASUREMENTS USING ELLIPTICALLY POLARIZED RADIATION

(75) Inventors: M. Pinar Mengüç, Lexington, KY (US); Sivakumar Manickavasagam, Albany, NY (US)

(73) Assignee: Synergetic Technologies, Inc., Rensselaer, NY (US)

( * ) Notice: Subject to any disclaimer, the term of this patent is extended or adjusted under 35 U.S.C. 154(b) by 76 days.

(21) Appl. No.: 09/956,388

(22) Filed: Sep. 19, 2001

(65) Prior Publication Data

US 2002/0057433 A1 May 16, 2002

Related U.S. Application Data

(60) Provisional application No. 60/234,061, filed on Sep. 20, 2000, and provisional application No. 60/233,864, filed on Sep. 20, 2000.

(51) Int. Cl.⁷ .................................................. G01J 4/00
(52) U.S. Cl. ........................ 356/368; 356/369; 356/367
(58) Field of Search ................................ 356/364–369; 250/225

(56) References Cited

U.S. PATENT DOCUMENTS

| 4,548,500 A | 10/1985 | Wyatt et al. |
| 4,616,927 A | 10/1986 | Phillips et al. |
| 4,693,602 A | 9/1987 | Wyatt et al. |
| 4,710,025 A | 12/1987 | Wyatt et al. |
| 4,735,504 A | 4/1988 | Tycko |
| 4,764,013 A | 8/1988 | Johnston |
| 4,884,886 A | 12/1989 | Salzman et al. |
| 4,889,690 A | 12/1989 | Opitz et al. |
| 4,953,978 A | 9/1990 | Bott et al. |
| 4,953,980 A | 9/1990 | DeVolk et al. |
| 4,989,978 A | 2/1991 | Groner |
| 5,037,202 A | 8/1991 | Batchelder et al. |
| 5,104,221 A | 4/1992 | Bott et al. |
| 5,416,588 A | 5/1995 | Ducharme et al. |
| 5,486,919 A | 1/1996 | Tsuji et al. |
| 5,515,163 A | 5/1996 | Kupershmidt et al. |
| 5,576,827 A | 11/1996 | Strickland et al. |
| 5,657,126 A | 8/1997 | Ducharme et al. |
| 5,788,632 A | 8/1998 | Pezzaniti et al. |
| 6,011,626 A * | 1/2000 | Hielscher et al. ............ 356/367 |
| 6,233,046 B1 * | 5/2001 | Alba et al. .................... 356/38 |

OTHER PUBLICATIONS

B.M. Agarwal and M.P. Menguc, "Forward and inverse analysis of single and multiple scattering of collimated radiation in an axisymmetric system," International Journal of Heat and Mass Transfer, vol. 34, No. 3, pp. 633–647, 1991.

S. Manickavasagam and M.P. Menguc, "Effictive Optical Properties of Pulverized Coal Particles as Determined from FT–IR Spectrometer Experiments," Energy and Fuel, vol. 7, No. 6, pp. 860–869, 1993.

(List continued on next page.)

Primary Examiner—Frank G. Font
Assistant Examiner—Layla Lauchman
(74) Attorney, Agent, or Firm—King & Schickli, PLLC

(57) ABSTRACT

A non-intrusive method of characterizing particles through inverse analysis of experimental data based on measurements using elliptically polarized radiation is provided. A database of theoretical absorption and scattering data sets for particles is compiled. Optimum settings for an experimental test to gather an experimental absorption and scattering data set are determined and the experimental test is conducted. The experimental absorption and scattering data set is then compared to the theoretical absorption and scattering data sets of the database of theoretical absorption and scattering data sets in order to determine an absorption and scattering data set which differs the least from the experimental absorption and scattering data set in order to characterize the particles.

59 Claims, 11 Drawing Sheets

OTHER PUBLICATIONS

M.P. Menguc, S. Manickacasagam and D.A. D'SA, "Determination of Radiative Properties of Pulverized Coal Particles from Experiments," FUEL, vol. 73, No. 4, pp. 613–625, 1994.

M.P. Menguc, A. Mahadeviah, et al., "Application of the Discrete Dipole Approximation to Determine the Radiative Properties of Soot Agglomerates," Heat Transfer in Fire and Combustion Systems ASME HTD–vol. 199, pp. 9–16, 1992.

B.M. Vaglieco, O. Monda, et al., "Optical and Radiative Properties of Particulates at Diesel Engine Exhaust," Combustion Science and Technology, vol. 102, pp. 283–299, 1994.

Z. Ivezic and M.P. Menguc, "An Investigation of Dependent/Independent Scattering Regimes Using a Discrete Dipole Approximation," International Journal of Heat Mass Transfer, vol. 39, No. 4, pp. 811–822, 1996.

Z. Ivezic, M.P. Menguc and T.G. Knauer, "A Procedure to Determine the Onset of Soot Agglomeration from Multi-wavelength Experiments," Journal of Quantitative Spectroscopy and Radiative Transfer, vol. 57, No. 6, pp. 859–865, 1997.

B. Bhanti, S. Manickavasagam and M.P. Menguc, "Identification of Non–Homogeneous Spherical Particles from their Scattering Matrix Elements," Journal of Quantitative Spectroscopy and Radiative Transfer, vol. 56, No. 4, pp. 591–608, 1996.

S. Manickavasagam and M.P. Menguc, "Scattering Matrix Elements of Fractal–like Soot Agglomerates," Applied Optics, vol. 36, No. 6, pp. 1337–1351, 1997.

S. Manickavasagam and M.P. Menguc, "Scattering–matrix Elements of Coated Infinite–length Cylinders," Applied Optics, vol. 37, No. 12, pp. 2473–2482, 1998.

S. Manickavasagam, R. Govindan, and M.P. Menguc, "Estimating the Morphology of Soot Agglomerates by Measuring their Scattering Matrix Elements," ASME International Mech. Eng. Congress and Exhibition, HTD–vol. 352, pp. 29–32, 1997.

B.M. Vaglieco, et al., "Optical and Radiative Properties of Particles at Diesel Engine Exhaust," Combust. Sci. and Tech., vol. 102, pp. 283–299, 1994.

M.P. Menguc and S. Manickavasagam, "Characterization of Size and Structure of Agglomerates and Inhomogeneous Particles via Polarized Light,." International Journal of Engineering Science, vol. 36, pp. 1569–1593, 1998.

Foeke Kuik, P. Stammes, and J.W. Hovenier, "Experimental Determination of Scattering Matrices of Water Droplets and Quartz Particles," Applied Optics, vol. 30, No. 33, pp. 4872–4881, 1991.

Randall C. Thompson, Jerold R. Bottiger, and Edward S. Fry, "Measurement of Polarized Light Interactions via the Mueller Matrix," Applied Optics, vol. 19, No. 8, pp. 1323–1332, 1980.

Roger J. Perry, Arlon J. Hunt, and Donald R. Huffman, "Experimental Determinations of Mueller Scattering Matrices for Nonspherical Particles" Applied Optics, vol. 17, No. 17, pp. 2700–2710, 1978.

* cited by examiner

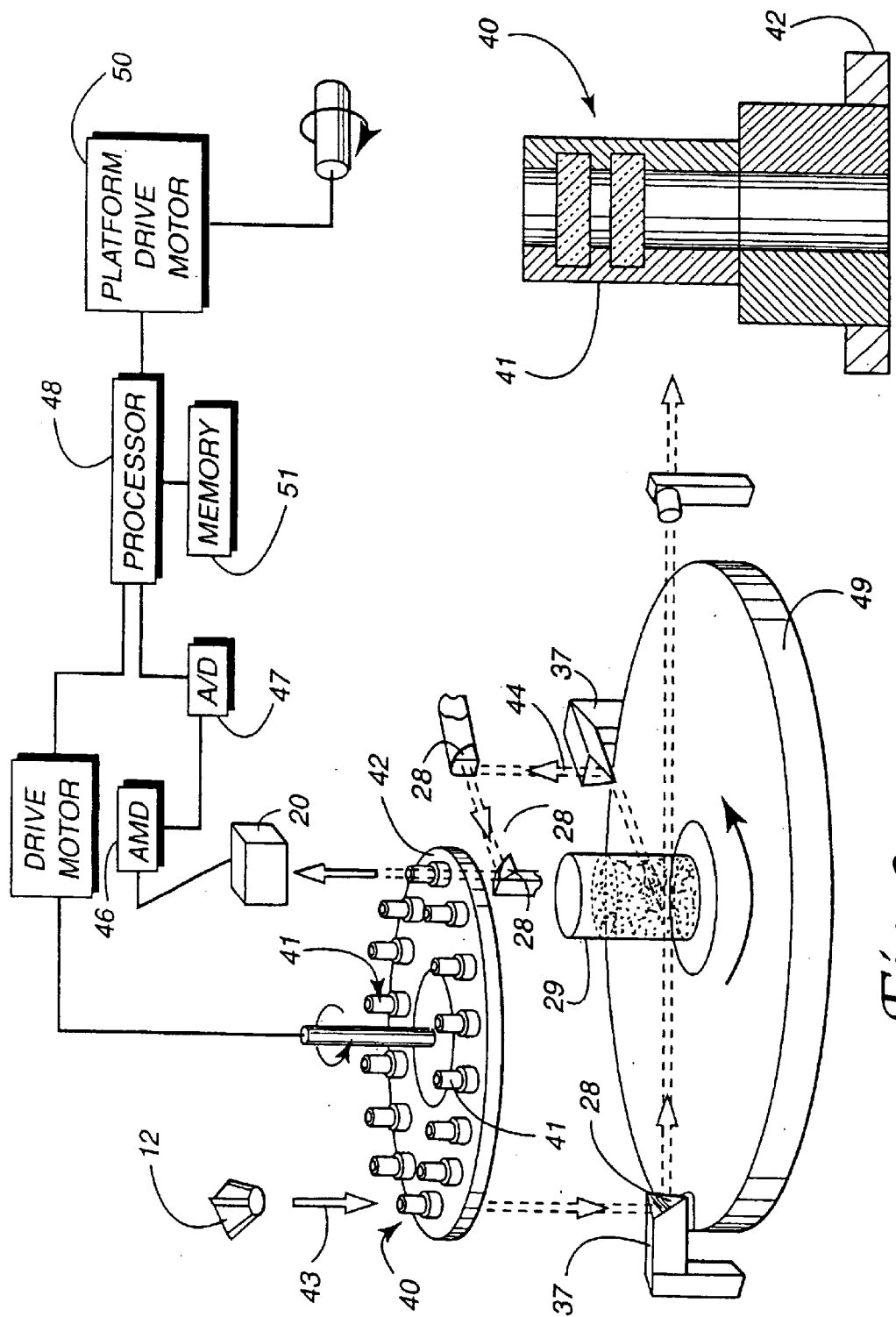

NON-INTRUSIVE METHOD AND APPARATUS FOR CHARACTERIZING PARTICLES BASED ON SCATTERING MATRIX ELEMENTS MEASUREMENTS USING ELLIPTICALLY POLARIZED RADIATION

This application claims the benefit of U.S. Provisional Application No. 60/234,061 and U.S. Provisional Application No. 60/233,864, both filed Sep. 20, 2000.

TECHNICAL FIELD

The present invention relates generally to particle characterization; and more particularly to an apparatus and non-intrusive methods for characterizing particles based on scattering matrix elements measurements made using elliptically polarized radiation, and methods of compiling a database of theoretical data for use therein.

BACKGROUND OF THE INVENTION

In many modern materials and manufacturing processes such as printers, copiers, fluidized bed reactors, powder coating machines, ceramic coatings, etc, small particles play a significant role. The control, streamlining and overall efficiency of many of these modern processes may be significantly improved if the particles involved in the processes are able to be precisely characterized. Determining whether particles resulting from a manufacturing process are spheroids as intended, for example, or whether the resulting particles actually agglomerated during the process may be critical to the overall success/efficiency of the process. These modern processes may be further enhanced by the ability to characterize particles such that the presence of undesirable particles and their respective adverse effects may be minimized. Examples of these processes include the fabrication of solid-state devices wherein the presence of sub-micron size contaminants in a fabrication area can have an enormous detrimental impact on the devices, metallurgical manufacturing wherein airborne dust particles create a significant fire and explosion hazard, and combustion chambers wherein a failure to burn soot particles including agglomerates allows their escape into the environment.

Recent advances in diverse disciplines, such as biological, pharmaceutical, environmental, and combustion systems as well as atmospheric and oceanographic remote sensing have created a much wider range of applications of and need for better characterization of particles in general. One of the most often used methods to characterize these particles includes optical diagnostics in which the particles are subjected to incident electromagnetic waves from a radiation source, and their responses or the scattered radiation are recorded. By comparing the recorded response against responses of previously physically measured particles, some characteristics of the particles may be estimated. These estimates, however, are only as accurate as the physically measured data which itself is difficult to accurately obtain at these small particle sizes. Although generally effective in confirming the presence of known or expected particle types, these methods of characterization are significantly limited and certainly may not be used to characterize unknown particle types and/or unexpected particles resulting from agglomeration during a process or the like.

Thus, as demonstrated by the limitations and disadvantages of the prior art methods of characterizing particles, there is a need identified for an improved more robust method of characterizing particles and mixtures of particles of any size, shape, and size and/or shape distribution without a reliance on measured data which is often unavailable, inaccurate, or incomplete for the particles being characterized.

SUMMARY OF THE INVENTION

The present invention meets these needs by providing a non-intrusive method of characterizing particles or particle systems through inverse analysis of experimental data based on measurements using elliptically polarized radiation. A database of theoretical absorption and scattering data sets for particles is compiled. Optimum settings for an experimental test to gather an experimental absorption and scattering data set are determined and the experimental test is conducted. The experimental absorption and scattering data set is then compared to the theoretical absorption and scattering data sets of the database of theoretical absorption and scattering data sets in order to determine an absorption and scattering data set which differs the least from the experimental absorption and scattering data set in order to characterize the particles.

The particles referred to throughout the present application are herein defined to include fine particles and/or agglomerates of any size, size distribution, and shape. More specifically, the fine particles may include homogeneous spheres, radially inhomogeneous spheres, homogeneous cylinders, radially inhomogeneous cylinders, oblate spheroids, prolate spheroids, and/or ellipsoids, hollow particles, nanostructures, and nanocrystals, and the agglomerates may include irregular shaped structures, fractal-like agglomerates, fluffy or compact agglomerates, and hollow particles.

In accordance with a first aspect of the present invention, the step of compiling the database of theoretical absorption and scattering data sets for the particles may include the steps of calculating an interaction of a theoretical incident planar wave having a wavelength ($\lambda$) on each monomer of the particle having a diameter (d) and a complex index of refraction (m=n–ik), and interactions of portions of the theoretical incident planar wave scattered by each remaining monomer of the particle using Maxwell's equations as is known in the art. The diameter (d) of each monomer may be an effective diameter based on a volume of the monomer. For irregular shaped particles, the particle may be divided into volumes which are themselves converted into effective spherical diameters. For the remaining particles types, the monomer diameter may be made equivalent to the size of the small spheres which make up the agglomerate or the like. The calculated interactions may then be summed for each monomer of the particle and a distribution of the theoretical incident planar wave scattered by the particle and an absorption of the theoretical incident planar wave by the particle determined. The method may further comprise the step of determining scattering matrix elements for the particle based on the determined distribution of the theoretical incident planar wave scattered by the particle and the determined absorption of the theoretical incident planar wave by the particle.

In accordance with another aspect of the present invention, the step of compiling the database of theoretical absorption and scattering data sets for the particles preferably includes the additional step of repeating the aforementioned steps of calculating an interaction of a theoretical incident planar wave and interactions of portions of the theoretical incident planar wave, summing the calculated interactions, determining a distribution of the theoretical incident planar wave scattered by the particles and an absorption of the theoretical incident planar wave by the particles, and determining scattering matrix elements for every possible combination of wavelength ($\lambda$), and particle characteristic including diameter (d), complex index of refraction (n), and absorption index (k). For particles which include fractal agglomerates, the aforementioned steps are further repeated for every possible combination of fractal dimension $D_f$ and prefactor $K_f$.

In accordance with still another aspect of the present invention, the step of determining optimum settings for the experimental test to gather the experimental absorption and scattering data set further includes the step of estimating characteristics of the particles being characterized. The estimated characteristics of the particles being characterized may include data obtained from a transmission electron microscope, a scanning electron microscope, or an atomic force microscope, for example. A wavelength of a theoretical elliptically polarized radiation is selected based on the estimated characteristics of the particles being characterized and a theoretical set of polarizers and retarders are selected based on the selected wavelength. The step of determining optimum settings may further include the step of selecting an orientation for optical axes of the polarizers and retarders in the theoretical set.

Utilizing the selected theoretical set of polarizers and retarders, an intensity of the theoretical elliptically polarized radiation scattered by the particles being characterized at a detection plane at different scattering angles may be determined. These steps may be repeated for each selected orientation of the polarizers and retarders in the theoretical set. Based on the intensity of the theoretical elliptically polarized radiation scattered by the particles, orientations for the optical axes of the polarizers and retarders in the theoretical set which provide sufficiently high signal-to-noise ratios may be selected as the optimum settings for use in the experimental test.

According to another aspect of the present invention, the step of determining optimum settings may further include the step of conducting a preliminary experimental test. The preliminary experimental test may be conducted when insufficient data is available regarding the characteristics of the particles being characterized, for example, when no information or data is available for the particles to be characterized or if the particles are composed of combinations of different particle types and information or data for the combination or at least some of the particle types which form the combination is unavailable.

As described above, the steps of selecting a wavelength of an elliptically polarized radiation based on a set of estimated characteristics of the particles being characterized, selecting a set of polarizers and retarders each having an optical axis based on the selected wavelength, and selecting an orientation for the optical axes of said polarizers and retarders in said set are similarly established prior to conducting the preliminary experimental test. Conducting the preliminary experimental test includes the steps of directing elliptically polarized radiation having the selected wavelength toward the particles to be characterized, modulating the polarization of the radiation before and after the radiation is incident on the particles, and detecting radiation scattered by the particles to be characterized at at least one scattering angle. The steps of directing, modulating, and detecting scattered radiation may be repeated any number of times sufficient to collect the necessary data. The orientation of the optical axes of the polarizers and retarders in the set are preferably adjusted prior to each repetition of the noted directing, modulating, and detecting steps.

The polarization of the radiation before and after the radiation is incident on the particles may be modulated utilizing appropriately positioned polarizers and retarders in the sets. Preferably, lenses, apertures, and additional polarizers and retarders may be utilized to direct or modulate the radiation either before or after the radiation is incident on the particles. An intensity of the modulated radiation may be detected using one or more detectors positioned at different scattering angles. The detector preferably generates an output dependent upon the intensity of the scattered radiation at the present scattering angle.

In accordance with yet another aspect of the present invention, equations representing the outputs of the detectors resulting from the preliminary experimental test may be solved simultaneously in order to determine the preliminary experimental absorption and scattering data set. The preliminary experimental absorption and scattering data set is then compared to the theoretical absorption and scattering data sets of the database in order to determine an absorption and scattering data set which differs the least from the preliminary experimental absorption and scattering data set.

According to yet another aspect of the present invention, the estimated characteristics of the particles being characterized may be replaced with new characteristics corresponding to the preliminary experimental absorption and scattering data set. Additionally, the preliminary experimental test and replacement of the estimated characteristics or the previous replacement characteristics may be repeated any number of times in order to improve the accuracy of the estimated characteristics for use in the step of determining the optimum settings.

In accordance with another aspect of the present invention, the step of conducting the experimental test may include the steps of directing elliptically polarized radiation having a selected wavelength toward the particles to be characterized, modulating the polarization of the radiation before and after the radiation is incident on the particles to be characterized, and detecting radiation scattered by the particles to be characterized at at least one scattering angle. The steps of directing, modulating, and detecting the elliptically polarized radiation are repeated six times in accordance with the present preferred method, however, the steps may be repeated fewer or more times depending on the type of particles or combinations of particles being characterized and/or the amount of information known about the particles.

As in the preliminary experimental test, the polarization of the radiation before and after the radiation is incident on the particles may be modulated utilizing appropriately positioned polarizers and retarders. Each of the polarizers and retarders have optical axes which are preferably established at a first predetermined orientation or optimum setting before conducting the experimental test. The optical axes of at least one of the polarizers and retarders may be adjusted to a second predetermined orientation between successive repetitions of the directing, modulating and detecting steps. The modulated radiation may be detected using one or more detectors positioned at different scattering angles. The detectors preferably generate an output based on the intensity of the detected radiation. Equations representing the outputs of the detectors resulting from the experimental test may be solved in order to determine an experimental absorption and scattering data set. The experimental absorption and scattering data set is then compared to the theoretical absorption and scattering data sets of the database in order to determine an absorption and scattering data set which differs the least from the preliminary experimental absorption and scattering data set.

In accordance with another aspect of the present invention, the step of conducting an experimental test may be repeated at least once utilizing elliptically polarized radiation having a different wavelength in order minimize errors. More specifically, repeating the experimental test utilizing radiation having a different wavelength avoids errors which may be contributed to particles having significant absorption properties at specific wavelengths. The first experimental data set may be compared to at least one subsequent data set in order to insure the integrity of the experimental data set to be compared to the theoretical absorption and scattering data sets of the database. If a discrepancy between the experimental data sets is determined, additional experimental tests may be conducted utilizing radiation having another different wavelength in order to determine which set of experimental data is not affected by the significant absorption of the incident radiation by the particles.

Additional error minimization techniques may also be utilized including correcting the outputs of the detectors to remove interface and multiple scattering effects which may cause modulation of the elliptically polarized radiation. This may be accomplished, for example, by multiplying the outputs of the detectors by a corrective function selected to remove the noted interface and multiple scattering effects as is known in the art.

Another non-intrusive method of characterizing particles through inverse analysis of experimental data based on measurements made using elliptically polarized radiation includes the steps of conducting an experimental test utilizing predetermined optimized settings to obtain an experimental absorption and scattering data set, and comparing the experimental absorption and scattering data set to theoretical absorption and scattering data sets of a database in order to determine an absorption and scattering data set which differs the least from the experimental absorption and scattering data set. Preferably, the database of theoretical absorption and scattering data sets for the particles being characterized and the optimum settings for the experimental test have been theoretically or experimentally predetermined.

According to a second aspect of the present invention, an apparatus for characterizing particles through a non-intrusive inverse analysis of experimental data based on measurements using elliptically polarized radiation comprises a radiation source for generating elliptically polarized radiation having a wavelength ($\lambda$), a plurality of polarizers and retarders each having an optical axis for modulating the elliptically polarized radiation before and after the radiation is incident on the particles, and at least one detector for detecting radiation scattered by the particles and generating an output. The apparatus further includes a controller for adjusting an orientation of the optical axis of at least one of the polarizers and retarders, and a processor for receiving the output from the detector, generating an experimental absorption and scattering data set based on the output of said at least one detector, and comparing the experimental absorption and scattering data set to theoretical absorption and scattering data sets in order to determine an absorption and scattering data set which differs the least from the experimental absorption and scattering data set in accordance with the above-described methods.

In accordance with another aspect of the present invention, the apparatus may include a rotary stage for supporting the particles, the polarizers and retarders, and/or the detector. Additionally, fiber optic cables and holders may be provided for directing the elliptically polarized radiation from the radiation source toward the particles and/or for collecting radiation scattered by the particles and modulated by the polarizers and retarders for directing to the detector. A motor such as stepper motor or other suitable motor may be provided for driving the rotary stage in response to control signals provided by the controller. In addition, the processor of the apparatus may be further programmed to generate the theoretical absorption and scattering data sets and/or determine an orientation for the polarizers and retarders in accordance with the methods described above.

In accordance with still another aspect of the present invention, a plurality of selectable polarizer and retarder sets may be mounted on a moveable platform controlled by the controller. In this alternate embodiment of the present preferred apparatus, an orientation of the optical axes of the polarizers and retarders in the polarizer and retarder sets mounted on the moveable platform are fixed. Rather than utilizing a controller to adjust the orientation of adjustable polarizers and retarders, the polarizers and retarders are selected by moving the platform based on their fixed orientations. In accordance with the broadest teachings of the present invention, any number of polarizer and retarder sets may be mounted on the moveable platform for selection by the processor.

Additional advantages, and other novel features of the invention will be set forth in part in the description that follows and in part will become apparent to those skilled in the art upon examination of the following or may be learned with the practice of the invention. The objects and advantages of the invention may be realized and attained by means of the instrumentalities and combinations particularly pointed out in the appended claims.

BRIEF DESCRIPTION OF THE DRAWINGS

The accompanying drawings incorporated in and forming a part of the specification, illustrate several aspects of the present invention, and together with the description serve to explain the principles of the invention. In the drawings:

FIG. 2 is an alternate apparatus for characterizing particles in a non-intrusive manner through inverse analysis of experimental data based on measurements using elliptically polarized radiation and selectable sets of modulators;

FIG. 3 is a cylindrical mount for a polarizer and retarder pair used in the alternate apparatus for characterizing particles in a non-intrusive manner through inverse analysis of experimental data based on measurements using elliptically polarized radiation.

Reference will now be made in detail to the present preferred embodiment of the invention, an example of which is illustrated in the accompanying drawings.

DETAILED DESCRIPTION OF THE PREFERRED EMBODIMENT

Figure 1:
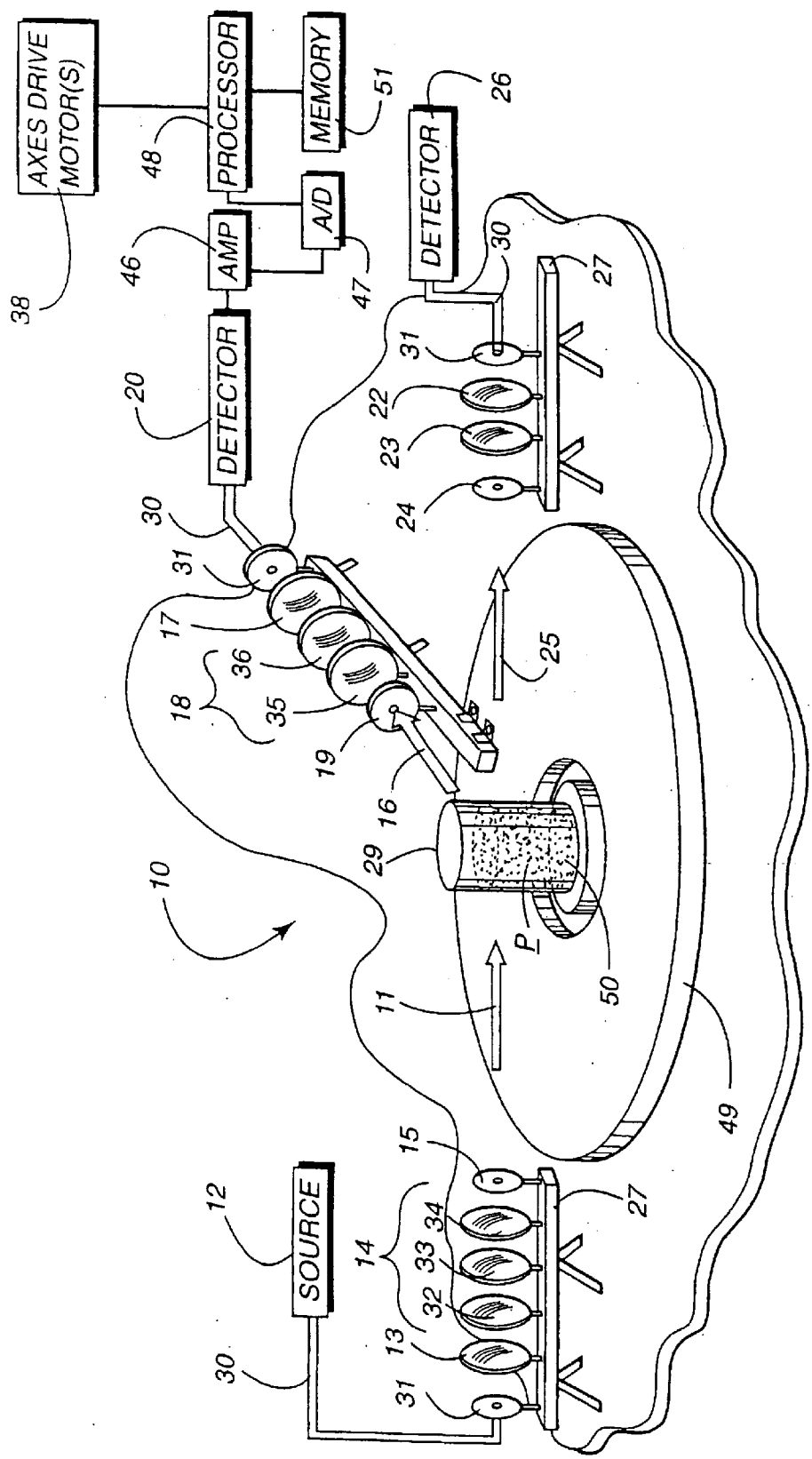
FIG. 1 is a preferred apparatus for characterizing particles in a non-intrusive manner through inverse analysis of experimental data based on measurements using elliptically polarized radiation and modulators having adjustable optical axis orientations.

With reference to the perspective view of FIG. 1, there is shown a preferred embodiment of an apparatus 10 for characterizing particles through inverse analysis of experimental data based on measurements using non-intrusive elliptically polarized radiation 11. The apparatus 10 includes a radiation source 12 for generating elliptically polarized radiation 11 having a selected wavelength (λ) and directing the elliptically polarized radiation toward the particles (P) being characterized. As further shown, the elliptically polarized radiation 11 is directed toward the particles (P) through a first bi-convex lens 13, combination of polarizers and retarders 14, and spatial filter 15 or pin hole before it is incident on the particles (P). After the radiation 11 is scattered and/or absorbed by the particles (P), portions of the scattered radiation 16 travel through a second spatial filter 19, combination of polarizers and retarders 18, and bi-convex lens 17 before their detection by a detector 20. A third spatial filter 24, combination of polarizers and/or retarders 23, and bi-convex lens 22 receive the transmitted radiation 25 before its detection by a transmitted radiation detector 26 for use in attenuation calculations. In the present preferred embodiment, each of the noted groupings of optical components may be supported by a suitable component rail 27 or the like and positioned within a suitable housing (not shown for clarity).

In accordance with the broadest aspects of the present invention, the apparatus 10 is capable of accurately characterizing particles or particle systems containing combinations of one or all of the above particle types and/or having any size distribution. Preferably, the overall size of the particles, i.e., the ratio of the perimeter of an effective spherical particle to the wavelength of the incident radiation ($x=\pi D/\lambda$) is not more than one order of magnitude smaller or larger than unity for the most effective utilization of the present invention. The particles (P) may be suspended in a solid or flowing in a liquid or a gas during the characterization process. Advantageously, this allows particle characterization to be conducted on-line during any type of manufacturing process, or in a more traditional and controlled laboratory setting. Most preferably, the particles (P) are suspended in a transparent solvent in a uniquely designed optical cell 29 which significantly reduces if not eliminates any backscattering of radiation from an outer surface of the cell.

The radiation source 12 for generating elliptically polarized radiation having a selected wavelength (λ) may be a commercially available laser, such as a Nd:YAG laser-optical parametric oscillator. Of course, other sources capable of generating elliptically polarized radiation may similarly be utilized including different types of laser sources or x-ray sources.

As shown in FIG. 1, the radiation source 12 is preferably remotely positioned such that the elliptically polarized radiation is transmitted along an optical path or cable 30 before being directed toward the particles (P) being characterized. Alternately, the radiation source 12 may be positioned such that the elliptically polarized radiation 11 generated by the radiation source is directed directly toward the particles being characterized. The optical path or cable 30 may include a group of forty-five degree prisms 28 or the like mounted on high precision adjustment tools 37 for directing the radiation along the path as shown in the alternate embodiment in FIG. 2 or a fiber optic cable 30 for guiding the radiation toward the particles as shown in FIG. 1. Most preferably, a fiber optic cable is terminated in a holder 31 adjacent to the first bi-convex lens 13, combination of polarizers and retarders 14, and spatial filter 15.

The ability to remotely position the radiation source 11 allows the apparatus 10 to operate in diverse environments where conditions such as constant or intermittent vibrations, for example, may interfere with the accuracy of the characterization process. By remotely positioning the radiation source 11, adequate protection against such conditions may be provided such as a vibrational damping means or the like, or the conditions typically encountered in these adverse environments may be nullified by mere proximity.

The elliptically polarized radiation 11 emerging from the fiber optic cable 30 is initially focused using the first bi-convex lens 13. The focused radiation is subsequently modulated by the first combination of polarizers and retarders 14 and its profile cleaned by the spatial filter 15 before it is incident on the particles (P). In the present preferred embodiment, the first combination of polarizers and retarders 14 includes a first polarizer 32 having a fixed orientation of its optical axis, a first half-wave retarder 33 having an optical axis and a retardance of $\lambda/2$, and a first quarter-wave retarder 34 having an optical axis and a retardance of $\lambda/4$. Preferably, an orientation of the optical axes of the first polarizer 32, and first half-wave and quarter-wave retarders 33, 34 are adjustable in order to optimize the apparatus 10 dependent upon estimated characteristics of the particles (P) being characterized. The process of optimizing the apparatus 10, and more particularly the orientation of the optical axes, will be discussed in more detail below. Alternately, the radiation emerging from the fiber optic cable 30 may be mechanically modulated, i.e., chopped, before being focused by the first lens 13.

After the radiation 11 is scattered and/or absorbed by the particles (P), the profile of the portions of the scattered radiation 16 is cleaned by the second spatial filter 19, and further modulated by the second half-wave retarder 35 and second polarizer 36. Preferably, an orientation of the optical axes of the second half-wave retarder 35 and second polarizer 36 is adjustable as in the first combination of polarizers and retarders 14 in order to optimize the apparatus 10 dependent upon estimated characteristics of the particles (P) being characterized. The modulated portions of the scattered radiation 16 are subsequently focused by the second bi-convex lens 17 and directed along an optical path toward the detector 20. As with the optical path associated with the radiation source 12, the optical path or cable associated with the detector 20 may include a group of forty-five degree prisms 28 or the like mounted on high precision adjustment tools 37 for directing the radiation portions along the path as shown in the alternate embodiment of FIG. 2 or a fiber optic cable 30 for guiding the radiation portions 16 toward the detector 20 as shown in FIG. 1. Most preferably, a fiber optic cable 30 is terminated in a holder 31 adjacent to the second bi-convex lens 17 for use in receiving the portions of the scattered radiation 16 and guiding the scattered radiation portions toward the detector 20.

Again, the ability to remotely position the detector 20 further supports operation of the apparatus 10 in diverse environments where conditions such as constant or intermittent vibrations may interfere with the accuracy of the characterization process. By remotely positioning the detector 20, adequate protection against such conditions may be provided or the conditions typically encountered in these adverse environments may be nullified by mere proximity.

In the present preferred embodiment, the orientations of the optical axes of each of the first half-wave and quarter-wave retarders 33, 34, the second half-wave retarder 35, and second polarizer 36 are adjustable throughout testing in accordance with predetermined optimum settings. In the present preferred embodiment, the adjustments of the polarizers and retarders are controlled utilizing drive motors 38 and appropriate drive mechanisms (the drive mechanisms and connections to the drive motors 38 are not shown). An example of such a drive mechanism is part number 13048, an encoded rotator manufactured by Oriel, Inc. Alternatively, the orientation of the optical axis of the polarizers and retarders may be hand adjustable. As indicated above, the process of determining the optimum settings and the timing of the adjustments will be described in detail below.

In accordance with an important aspect of the present invention, adjusting the orientation of the optical axes of each of the first half-wave and quarter-wave retarders and the second half-wave retarder and second polarizer provides a variable ellipticity of the incident radiation and portions of the scattered radiation. By adjusting the orientation of the optical axes, the portions of the scattered radiation detected by the detector are assured of providing data for the necessary elements of a particle scattering matrix as will be described in greater detail below.

In the alternate embodiment shown in FIG. 2, the polarizers and retarders utilized to modulate the incident radiation and portions of the scattered radiation may have fixed optical axes. In such an alternate embodiment, several polarizer and retarder pairs 40 are required due to the lack of adjustability. Preferably, twelve to twenty cylindrical mounts 41 are provided on a circular platform 42 for receiving the polarizer and retarder pairs 40 as best shown in FIG. 3. The polarizer and retarder pairs 40 are positioned around the circular platform 42 for selectively positioning the different pairs in the path of the incident radiation 43 and portions of the scattered radiation 44 dependent upon the desired angle of optical axes.

In the present preferred and alternate embodiments, the detector 20 is provided for detecting the portions of the radiation scattered by the particles and generating an output. Most preferably, the detector 20 is an optical detector which may be a photo multiplier tube, an avalanche photodiode, or a charge coupled device, for example, capable of generating an output voltage which is indicative of an intensity of the portions of the scattered radiation received by the detector. Data collected from the detector 20 may be transmitted to a voltage or current amplifier 46 (shown in FIG. 1) if the incident elliptically polarized radiation is unchopped or a lock-in amplifier if the radiation is chopped. Once amplified, the data is converted utilizing an A/D converter 47 before reaching a data acquisition system within the control processor 48 where the data is gathered using an acceptable data acquisition software application known in the art, and processed on demand.

The particle cell 29 is mounted on a circular platform or rotary stage 49. The platform 49 is rotationally driven by a processor 48 controlled stepper motor 50 or other suitable motor to vary the scattering angle at which the portions of the scattered radiation 16 are received or detected. As shown in FIG. 1, the second bi-convex lens 17, combination of polarizers and retarders 18, and spatial filter 19 are preferably mounted on the second optical component rail 27 which is in turn mounted to the platform 49 for rotation therewith. As will be described in more detail below, the portions of the scattered radiation 16 are preferably received by the fiber optic cable 30 or detected by the detector 20 along a range of scattering angles throughout the characterization process. Of course, the range of scattering angles may be between 0° and 360°, however, a more practical range which provides sufficient data to allow for the characterization of particles may be from 0° to 180°.

In yet another alternate embodiment, a plurality of detectors or even a plurality of fiber optic cables and at least one detector may be utilized in accordance with the broad teaching of the present invention, thus eliminating the need for a rotary stage. The plurality of detectors, for example, may be positioned along a range of scattering angles for receiving the portions of the scattered radiation. Of course, the detector would necessarily provide individual or multiplexed outputs to the data acquisition system within the control processor 48.

As indicated above, the control processor 48 controls the rotation of the rotary platform 49, adjustments to the orientation of the optical axes of the polarizer and retarder combinations 14 and 18 thru the drive motors 38, and receives data from the detector 20 utilizing the data acquisition software application. The control processor 48 is further programmed to generate an experimental absorption and scattering data set based on the acquired output data, and to compare the experimental absorption and scattering data set to theoretical absorption and scattering data sets in order to determine an absorption and scattering data set which differs the least from the experimental absorption and scattering data set as is described in more detail below. In the present preferred embodiment, the processor 48 is further programmed to generate theoretical absorption and scattering data sets and to determine optimum settings for the experimental test which may be stored in any type of memory device 51. For example, the memory device 51 may be internal to the processor 48 or an external device such as a disk drive, a tape drive, or a CD ROM drive, etc. may be utilized.

Figure 4:
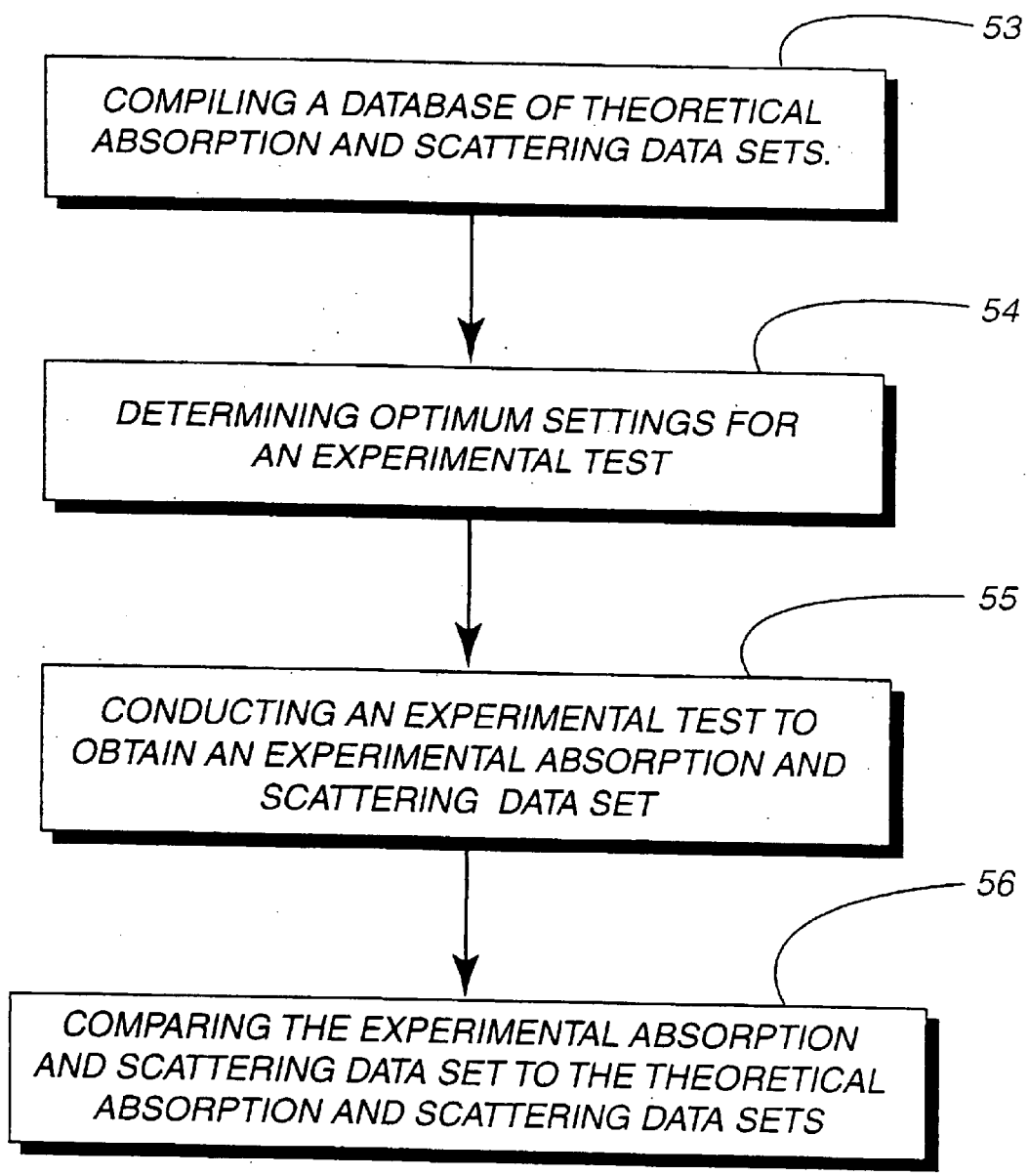
FIG. 4 is a software algorithm flowchart for a non-intrusive method of characterizing particles through inverse analysis of experimental data based on measurements using elliptically polarized radiation.

In operation, the apparatus 10 characterizes the particles (P) through inverse analysis of experimental data based on measurements using utilizing non-intrusive elliptically polarized radiation. As shown in the flowchart of FIG. 4, particle characterization is achieved by compiling a database of theoretical absorption and scattering data sets for the particles to be characterized in step 53, determining optimum settings for an experimental test to gather an experimental absorption and scattering data set in step 54, conducting the experimental test to obtain the experimental absorption and scattering data set in step 55, and comparing the experimental absorption and scattering data set to the theoretical absorption and scattering data sets of the database in step 56 in order to determine an absorption and scattering data set which differs the least from the experimental absorption and scattering data set.

Figure 5:
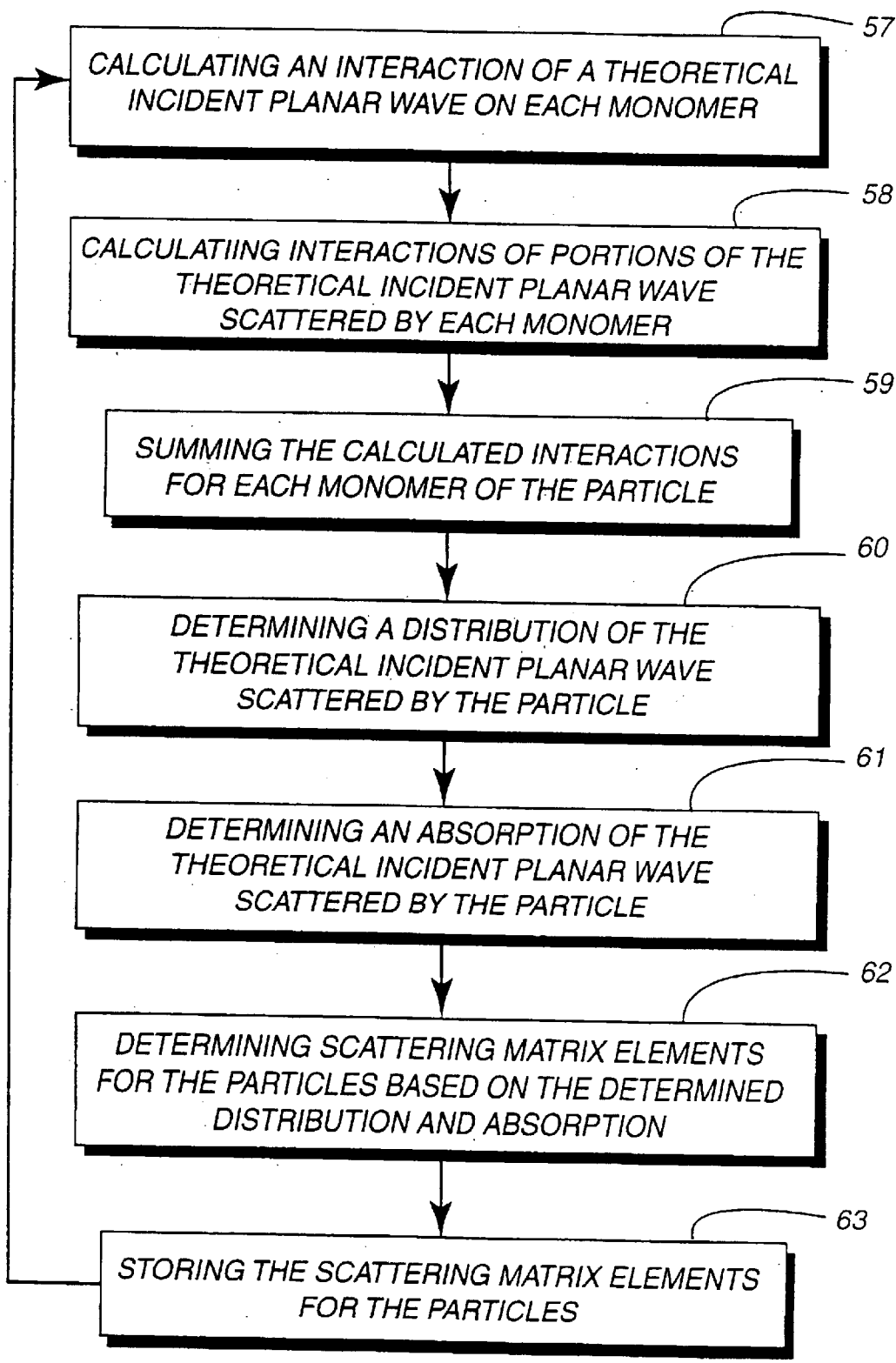
FIG. 5 is a software algorithm flowchart for compiling a database of theoretical absorption and scattering data sets.

In accordance with an important aspect of the present invention, the step 53 of compiling a database of theoretical absorption and scattering data sets for the particles (P) to be characterized is preferably accomplished utilizing a computer software algorithm the steps of which are set forth in FIG. 5. Specifically, the algorithm calculates an interaction of a theoretical incident planar wave having a wavelength ($\lambda$) on each monomer of a particle having a diameter (d) and a complex index of refraction (m=n−ik) in step 57, and interactions of portions of the theoretical incident planar wave scattered by each remaining monomer of the particle using Maxwell's equations in step 58 as is known in the art. In this manner, each sphere or effective sphere which makes up the theoretical particle is exposed not only to the theoretical incident planar wave but also the portions of the theoretical incident planar wave scattered by each remaining monomer. In order to account for the effective scattering cross-section and phase function of the particle, the calculated interactions are summed for each monomer of the particle in step 59 using methods generally known in the art.

In addition, the algorithm determines a distribution of the theoretical incident planar wave scattered in step 60 by the particles and an absorption of the theoretical incident planar wave by the particles in step 61. The determination is based on the direction of the incident beam and properties used in a manner generally known in the art. Based on this theoretical data, scattering matrix elements for the theoretical particles may be determined in step 62 based on the distribution of the theoretical incident planar wave scattered by the particles and the determined absorption of the theoretical incident planar wave by the particles.

In accordance with the broadest aspects of the present invention, the algorithm stores the scattering matrix elements in memory in step 63 and repeats the steps of calculating an interaction of a theoretical incident planar wave and interactions of portions of the theoretical incident planar wave, summing the calculated interactions, determining a distribution of the theoretical incident planar wave scattered by the particles and an absorption of the theoretical incident planar wave by the particles, and determining scattering matrix elements for the particles for every possible combination of wavelength ($\lambda$), diameter (d), complex index of refraction (n), and absorption index (k). If the particle is an agglomerate, additional characteristics may be required including a fractal dimension $D_f$, a prefactor $K_f$, and a fluffy or compact dimension (Fd). Again, the algorithm calculates scattering matrix elements for every possible theoretical particle and combination of particles having different sizes, size distributions, and structures.

In practice, some reasonable limitations on the range of the characteristics may be utilized to limit the possible number of different theoretical particles and combinations of particles, the size of the database, and processing time required to compare the experimental absorption and scattering data set to the theoretical absorption and scattering data sets of the database in order to determine an absorption and scattering data set which differs the least from the experimental absorption and scattering data set. For example, the theoretical incident planar wave may be limited to a wavelength ($\lambda$) between 190 and 2000 nanometers, the diameter (d) of the monomers may be between 5 and 400 nanometers, the absorption index (k) may be up to and including 5, the complex index of refraction (n) greater than 1, and the fractal dimension ($D_f$) of the fractal agglomerate may be greater than 1, and possibly between 1 and 3.

Further reductions in the size of the database of theoretical absorption and scattering data sets and necessarily processing times may be accomplished through the utilization of any available information about the physical characteristics of the particles or combinations of particles being characterized including size, size distribution, and shape. This may be of increased importance for on-line monitoring of particles in a manufacturing process where real time data is critical.

In addition to the theoretical absorption and scattering data sets obtained through the algorithm, additional absorption and scattering data sets for particles may be obtained from experimentation or different computer algorithms and simply added to the database. For example, the inventors of the present application have outlined the angular dependence of scattering matrix elements of radially-inhomogeneous spherical particles and agglomerates in a series of published articles including: (1) M. P. Mengüç and S. Manickavasagam, *Characterization of Size and Structure of Agglomerates and Inhomogeneous Particles via Polarized Light*, INTN'L Journal of Engineering Science, at 404, 1998; (2) S. Manickavasagam and M. P. Mengüç, *Scattering Matrix Elements of Fractal-like Soot Agglomerates*, Applied Optics, 36(6), 1337–1351, 1997; (3) D. Bhanti ET AL., *Identification of Non-homogeneous Spherical Particles from Their Scattering Matrix Elements*, Journal of Quantitative Spectroscopy and Radiative Transfer, Vol. 56, No. 4, 591–608, 1996; and (4) M. P. Mengüç and S. Manickavasagam, *Scattering Matrix Elements of Coated Infinite-Length Cylinders*, Applied Optics, Vol. 36, No. 6, 1337–1351, 1997 each incorporated herein by reference.

Figure 6:
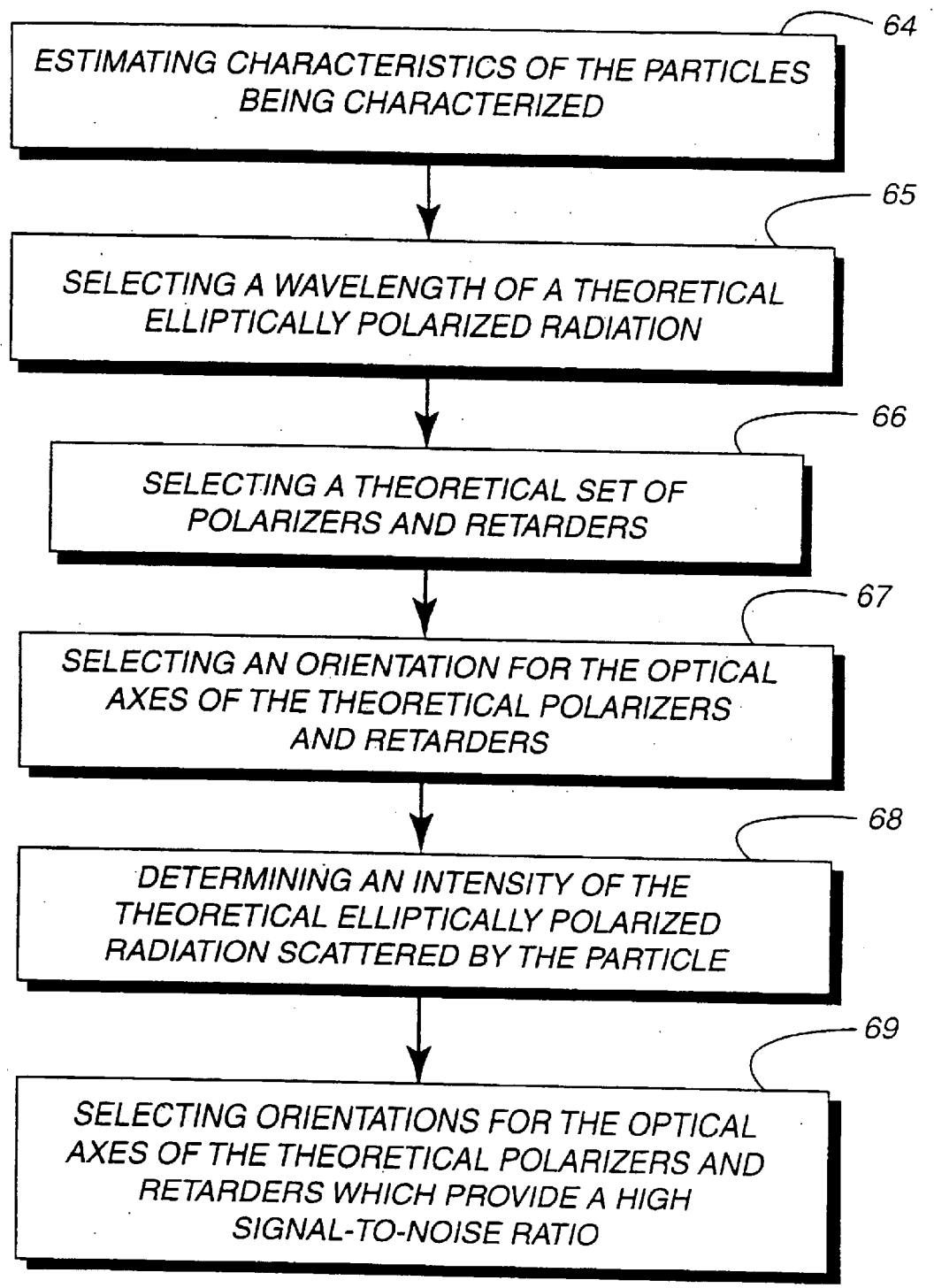
FIG. 6 is a software algorithm flowchart for determining optimum settings for an experimental test.

In accordance with another important aspect of the present invention as represented by the FIG. 6 flowchart, optimum settings for the experimental test to obtain the experimental absorption and scattering data set are calculated or determined based on an estimated set of physical characteristics of the particles being characterized as described above. The estimated set of physical characteristics may be based on any available data concerning the particles or combinations of particles being characterized. In most cases, the size, size distribution, and shape of particles which result from a target manufacturing process or the like or which may be harmful in a particular process are known and general information about their characteristics readily available.

Alternately or in addition thereto, the estimated characteristics may include data obtained utilizing any known measuring device including, for example, a transmission electron microscope, a scanning electron microscope, and an atomic force microscope. Even further, if no known data concerning the physical characteristics of the particles or combinations of particles being characterized is available, then a set of physical characteristics may be estimated in step 64.

The next step 65 in determining the optimum settings for the experimental test includes selecting a wavelength of a theoretical elliptically polarized radiation based on the estimated characteristics of the particles being characterized. Once the wavelength of the theoretical radiation is selected, theoretical polarizers and retarders are selected is step 66 based on the selected wavelength of the theoretical radiation. Next, an orientation for the optical axes of the polarizers and retarders in the theoretical set is selected in step 67.

Based on the known theoretical properties including the characteristics of the particle, the wavelength of the theoretical radiation, and the orientation of the polarizers and retarders, an intensity of the portions of the theoretical elliptically polarized radiation scattered by the particle or combination of particles being characterized at a detection plane at at least one scattering angle may be calculated or determined in step 68. Again, this calculation can be made for every scattering angle and at any interval if desired. For practical purposes, for example, a smaller sample may be determined along a range of between 0° and 180° at 1° intervals. The optimum settings are preferably selected in step 69 based on the orientations of the optical axes of the polarizers and retarders in the theoretical set which provide the highest intensity, or in other words, the theoretical set of polarizers and retarders which provide a sufficiently high signal-to-noise ratio. In accordance with the present preferred method, at least six optimum settings or orientations for the optical axes of the polarizers and retarders in the theoretical set are selected for use in the experimental test. However, fewer or more optimum settings for the optical axes may be selected depending on the type of particles being characterized and/or the amount of information known about the particles.

In the present preferred embodiment, the control processor 48 calculates or determines the optimum settings for the experimental test. In accordance with the broadest teachings of the present invention, the optimum settings for particles or combinations of particles having any combination of size, size distribution, and shape can be pre-calculated and stored in a database in a memory device 51 for later retrieval. Once the physical characteristics of the theoretical particles being characterized are estimated and the wavelength of the theoretical radiation is selected, the processor 48 may simply retrieve the optimum settings corresponding to the estimated physical characteristics and selected wavelength from the memory device 51.

Figure 7:
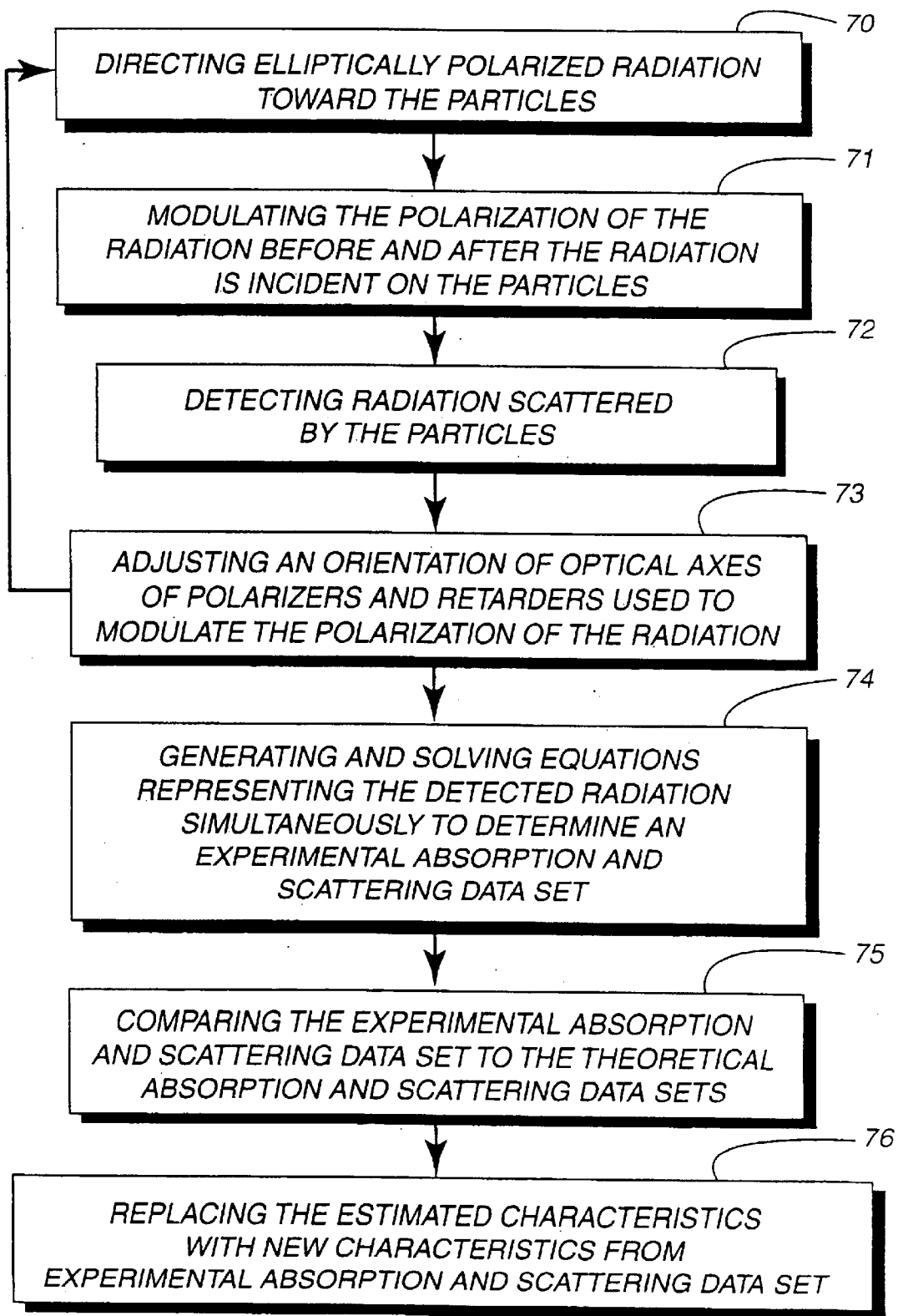
FIG. 7 is a software algorithm flowchart for an alternative method for determining optimum settings for an experimental test including conducting a preliminary experimental test.

An additional step which may be used in determining the optimum settings includes conducting a preliminary experimental test. The preferred steps of conducting a preliminary experimental test are shown in FIG. 7 and may include the steps of directing elliptically polarized radiation having the selected wavelength toward the particles (P) to be characterized in step 70, modulating the polarization of the radiation before and after the radiation is incident on the particles in step 71, and detecting portions of the radiation scattered by the particles to be characterized at at least one scattering angle in step 72. The steps of directing, modulating, and detecting scattered radiation may be repeated any number of times sufficient to collect the necessary data and the orientation of the optical axes of the polarizers and retarders in the set are preferably adjusted in step 73 prior to each repetition of the noted directing, modulating, and detecting steps.

The polarization of the radiation before and after the radiation is incident on the particles (P) may be modulated utilizing the polarizers 32, 36 and retarders 33, 34, 35 in the set positioned before and after the radiation is incident on the particles. An intensity of the modulated radiation may be detected using one or more detectors 20 positioned at different scattering angles. The detector 20 preferably generates an output dependent upon the intensity of the scattered radiation at the present scattering angle.

Once sufficient data is collected, equations representing the outputs of the detectors resulting from the preliminary experimental test may be generated and solved simultaneously in order to determine the preliminary experimental absorption and scattering data set in step 74. The preliminary experimental absorption and scattering data set is then compared in step 75 to the theoretical absorption and scattering data sets of the database in order to determine an absorption and scattering data set which differs the least from the preliminary experimental absorption and scattering data set.

The estimated characteristics of the particles or combinations of particles being characterized in step 64 may be replaced in step 76 with new characteristics corresponding to the preliminary experimental absorption and scattering data set. Additionally, the preliminary experimental test and replacement of the estimated characteristics or the previous replacement characteristics may be repeated any number of times in order to improve the accuracy of the estimated characteristics for use in the step of determining the optimum settings.

Figure 8:
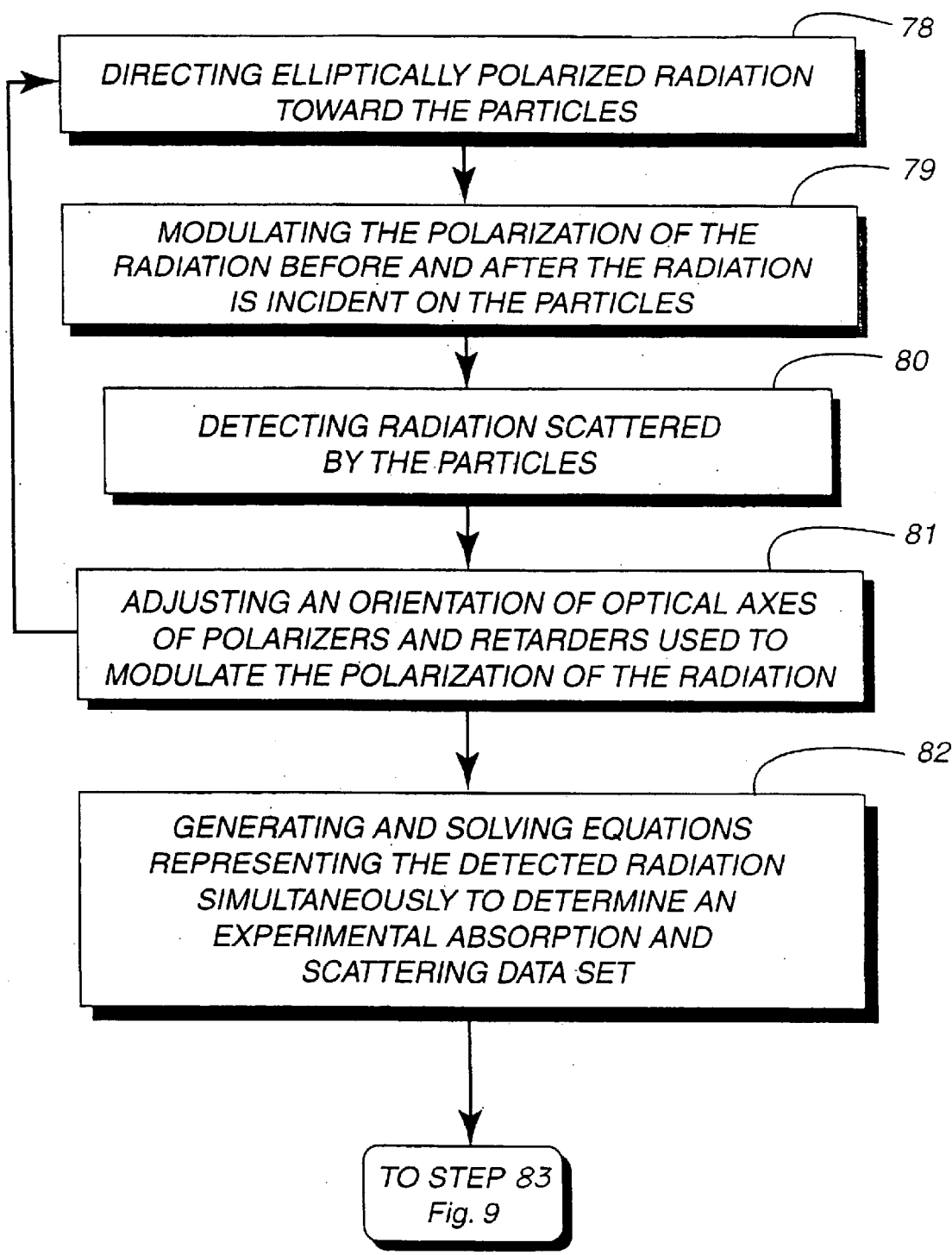
FIGS. 8 and 9 are a software algorithm flowchart for conducting an experimental test to obtain an experimental absorption and scattering data set.

In accordance with another aspect of the present invention, the step 55 of conducting the experimental test in FIG. 4 may include directing elliptically polarized radiation having a selected wavelength toward the particles to be characterized in step 78, modulating the polarization of the radiation before and after the radiation is incident on the particles to be characterized in step 79, and detecting radiation scattered by the particles to be characterized at at least one scattering angle in step 80 of FIG. 8. The steps of directing, modulating, and detecting the elliptically polarized radiation are most preferably repeated six times, however, the steps may be repeated fewer or more times depending on the type of particles being characterized and/or the amount of information known about the particles.

As in the preliminary experimental test, the polarization of the radiation before and after the radiation is incident on the particles (P) may be modulated utilizing the polarizers 32, 36 and retarders 33, 34, 35 positioned before and after the radiation is incident on the particles. Each of the polarizers and retarders have optical axes which are preferably established at a first predetermined orientation or optimum setting before conducting the experimental test. The optical axes of at least one of the polarizers 32, 36 and retarders 33, 34, 35 may be adjusted in step 81 to a second predetermined orientation between successive repetitions of the directing, modulating and detecting steps. The modulated radiation may be detected using one or more detectors 20 positioned at different scattering angles. The detectors 20 preferably generate an output based on the intensity of the detected radiation.

Equations representing the outputs of the detectors 20 resulting from the experimental test may be solved in step 82 in order to determine an experimental absorption and scattering data set. The experimental absorption and scattering data set is then compared to the theoretical absorption and scattering data sets of the database in step 56 of FIG. 4 in order to determine an absorption and scattering data set which differs the least from the preliminary experimental absorption and scattering data set.

Figure 9:
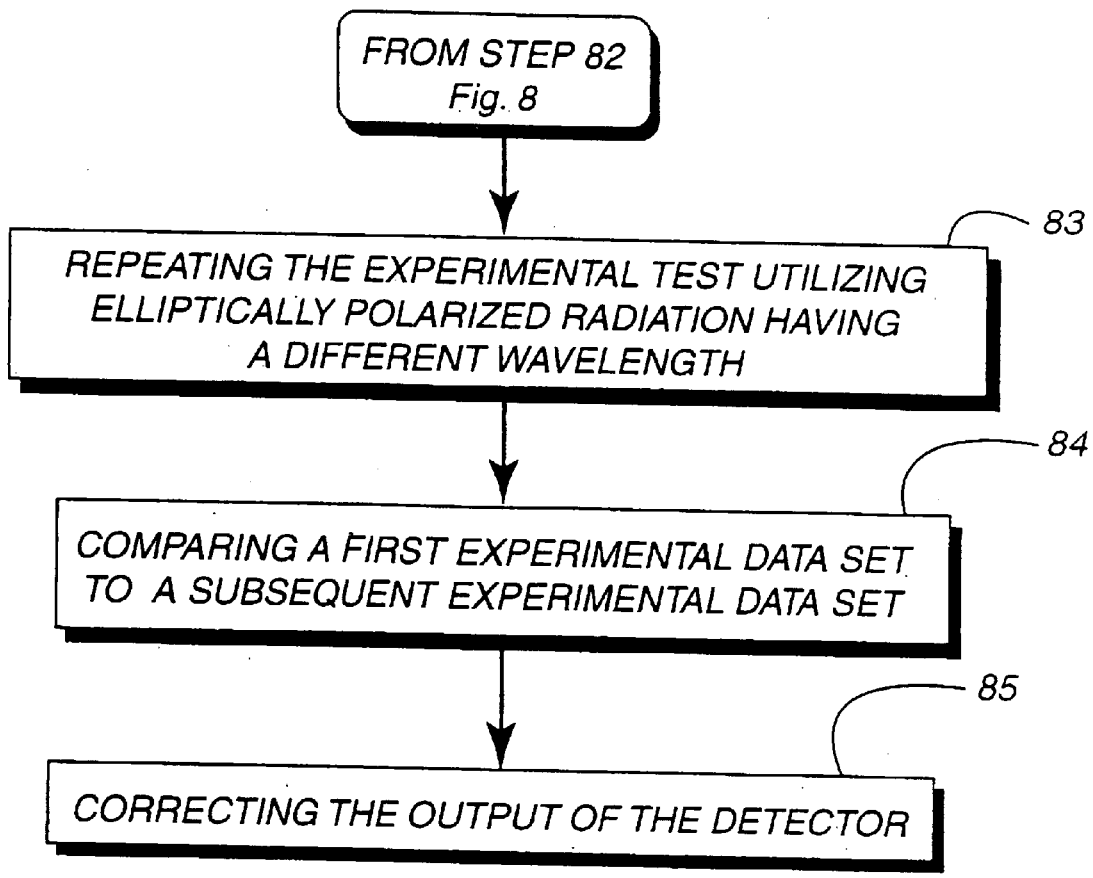

In accordance with another aspect of the present invention, the step 55 of conducting an experimental test may be repeated at least once utilizing elliptically polarized radiation having a different wavelength in order minimize errors as shown in step 83 of FIG. 9. More specifically, repeating the experimental test utilizing radiation having a different wavelength avoids errors which may be contributed to particles having significant absorption properties at specific wavelengths. The first experimental data set may be compared to at least one subsequent data set in order to insure the integrity of the experimental data set to be compared in step 84 to the theoretical absorption and scattering data sets of the database. If a discrepancy between the experimental data sets is determined, additional experimental tests may be conducted utilizing radiation having a different wavelength in order to determine which set of experimental data is not affected by significant absorption of the incident radiation by the particles.

Additional error minimization techniques may also be utilized including correcting the outputs of the detectors in step 85 to remove interface and multiple scattering effects which may cause modulation of the elliptically polarized radiation. This may be accomplished, for example, by multiplying the outputs of the detectors by a corrective function selected to remove the noted interface and multiple scattering effects.

In accordance with the theory behind the scattering matrix approach, the intensity and state of polarization of a beam of light can be completely specified by the following four-element Stokes vector:

$$[K] = [IQUV]^{-1} \quad (1)$$

where I represents the total intensity, Q the difference between the horizontally and vertically polarized intensities, U the difference between the +45° and −45° intensities, and V the difference between the right-handed and left-handed circularly polarized intensities.

The interaction of an optical device with a beam of light can be described as a transformation of an incident Stokes vector $K_i$ into an emerging Stokes vector $K_0$:

$$[K_0] = [S][K_i] \quad (2)$$

where [S] is the 4×4 matrix known as the Mueller or scattering matrix. It is characteristic of the optical device and those representing linear retarders and polarizers are easily derived. The transformation of an incident Stokes vector by a sequence of optical devices is given by the matrix that is the sequential product of the matrices representing each optical device. In one embodiment of the present invention, for example, the transformation from the incident Stokes vector to the emergent Stokes vector can be written as:

$$[K_0] = [P_2][R_3][S(\Theta)][R_2][R_1][P_1][K_i] \quad (3)$$

The Mueller matrices for an ideal linear polarizer [P] and a retarder [R] are given as:

$$[P] = \frac{1}{2} \begin{bmatrix} 1 & \cos 2\varepsilon & \sin 2\varepsilon & 0 \\ \cos 2\varepsilon & \cos^2 2\varepsilon & \cos 2\varepsilon \sin 2\varepsilon & 0 \\ \sin 2\varepsilon & \cos 2\varepsilon \sin 2\varepsilon & \sin^2 2\varepsilon & 0 \\ 0 & 0 & 0 & 0 \end{bmatrix} \text{ and} \quad (4)$$

$$[R] = \frac{1}{2} \begin{bmatrix} 1 & 0 & 0 & 0 \\ 0 & C^2 + D^2 \cos\delta & CD(1-\cos\delta) & -D\sin\delta \\ 0 & CD(1-\cos\delta) & D^2 + C^2 \cos\delta & C\sin\delta \\ 0 & D\sin\delta & -C\sin\delta & \cos\delta \end{bmatrix} \quad (5)$$

where $C = \cos 2\beta$; and $D = \sin 2\beta$. Here $\xi$ is the angle between the transmission axis of the polarizer and the parallel axis of the incident beam, $\beta$ is the angle between the parallel axis of the retarder and the horizontal, and $\delta$ is the retardance angle of a retarder. For quarter wave plates, the $\delta$ angle is 45° whereas for half-wave plates it is 90°. Of course, the orientation angle of the polarizer, $\xi$, can be set freely during the experiments. The proper choices for $\xi$ and $\beta$ angles depend on the condition number, CN, of the matrix inversion scheme, as discussed below.

The scattering matrix $[S(\theta)]$ for a single particle is written in the general form as:

$$[S(\theta)] = \frac{1}{k^2 r^2} \begin{bmatrix} S_{11} & S_{12} & S_{13} & S_{14} \\ S_{21} & S_{22} & S_{23} & S_{24} \\ S_{31} & S_{32} & S_{33} & S_{34} \\ S_{41} & S_{42} & S_{43} & S_{44} \end{bmatrix} \quad (6)$$

where $\theta$ is the scattering angle, $k = 1/\lambda$ is the wavenumber, and r is the distance from the center of the sample to the detector. Note that each of the matrix elements is a function of the scattering angle $\theta$. The scattering matrix for a cloud or system of particles is the sum of the individual scattering matrices for each of the particles.

For a cloud of particles that have a plane of symmetry and are randomly oriented, the Mueller matrix reduces to the following:

$$[S(\theta)] = \frac{1}{k^2 r^2} \begin{bmatrix} S_{11} & S_{12} & 0 & 0 \\ S_{21} & S_{22} & 0 & 0 \\ 0 & 0 & S_{33} & S_{34} \\ 0 & 0 & -S_{43} & S_{44} \end{bmatrix} \quad (7)$$

For example, soot particles/agglomerates in flames are randomly oriented: therefore, they have a plane of symmetry. The same argument applies to most particle systems. If particles in a sample have a preferential orientation, then the matrix elements should be calculated to take into account that orientation.

The Mueller matrices corresponding to the polarizers and retarders (given by equations (4) and (5) above) and the cloud of particles (given by equation (7) above) are substituted into equation 3 to obtain the output Stokes vector.

To determine the recommended values of angles for polarizers and retarders, we must look at the expression for $I_0$ which contains a combination of various terms involving sines and cosines of the orientation angles $\xi_1$, $\xi_2$, $\beta_1$, $\beta_2$, and $\beta_3$ of retarders and polarizers and the Mueller matrix elements of the particle cloud (from equation (7) above). Since we are interested in identifying six Mueller matrix elements, we have to have six independent equations, which can be obtained by using six different sets of the orientation angles, $\xi_1$, $\xi_2$, $\beta_1$, $\beta_2$, and $\beta_3$ of retarders and polarizers. The system of equations obtained can be written in matrix form as $$[C][Z] = [B] \quad (8)$$

where $$[Z] = \begin{bmatrix} S_{11} \\ S_{12} \\ S_{22} \\ S_{33} \\ S_{34} \\ S_{44} \end{bmatrix}$$

Here [C] is the coefficient matrix consisting of the coefficients of the Mueller matrix elements obtained and the elements of [B] correspond to the intensities obtained from measurements with six different orientation angles of polarizers and retarders. The multiplicative constant in the expression for the intensity is $(I_i + U_i)/(k^2 r^2)$. Since we do not necessarily know $I_i$ and $U_i$ values, we prefer to normalize the measured intensities with an additional intensity measured using particles of known size and refractive index.

The optimum combinations of angles, $\xi_1$, $\xi_2$, $\beta_1$, $\beta_2$, and $\beta_3$ of retarders and polarizers were determined following the procedure set forth by Govindan et al. in Govindan ET AL., *Identification of Characteristics of Soot Agglomerates from Polarization Experiments*, MSME Thesis, Department of Mechanical Engineering, University of Kentucky, Lexington, Ky. incorporated herein by reference. This set of optimum angles and the corresponding elements of the coefficient matrix [C] are given in Tables 2 and 3 below. It is to be noted that this choice is not unique: many other optimum conditions can be found such that the condition number of [C] is less than 10.

TABLE 2

Set of Optical Component Angles which Yields CN < 10 (CN = 9.58)

| $\xi_1$ | $\xi_2$ | $\beta_1$ | $\beta_2$ | $\beta_3$ |
|---|---|---|---|---|
| 45 | 80 | 70 | 60 | 80 |
| 45 | 20 | 30 | 20 | 10 |
| 45 | 30 | 0 | 30 | 40 |
| 45 | 70 | 50 | 10 | 10 |
| 45 | 0 | 70 | 30 | 0 |
| 45 | 50 | 60 | 80 | 60 |

TABLE 3

Coefficient Matrix [C] for Optical Component Angles given in Table 2

| 1.000000 | −1.110702 | 0.160697 | 0.101307 | −0.321395 | 0.000000 |
| 1.000000 | 1.637427 | 0.666157 | 0.203449 | −0.160696 | 0.059392 |
| 1.000000 | −0.269836 | −0.070658 | −0.694061 | 0.206194 | −0.171010 |
| 1.000000 | −0.469842 | −0.000001 | 0.000000 | 0.171008 | −0.866026 |
| 1.000000 | 0.678607 | −0.321393 | 0.000000 | 0.000000 | 0.000000 |
| 1.000000 | −1.395259 | 0.434801 | 0.274109 | 0.256517 | −0.059392 |

The present method of characterizing particles through inverse analysis of experimental data based on measurements using elliptically polarized radiation was utilized in the characterization of particles or combinations of particles of known size, shape, and optical properties. In a first experiment, latex polystyrene microspheres, supplied by Duke Scientific, were used to test and validate the preferred method. In the test, four different sizes of latex spheres were characterized having average diameters of 50 nm, 100 nm, 453 nm, and 900 nm. The size of the latex spheres were measured by standard techniques (NIST Standards) and supplied by the manufacturer.

Figure 10:
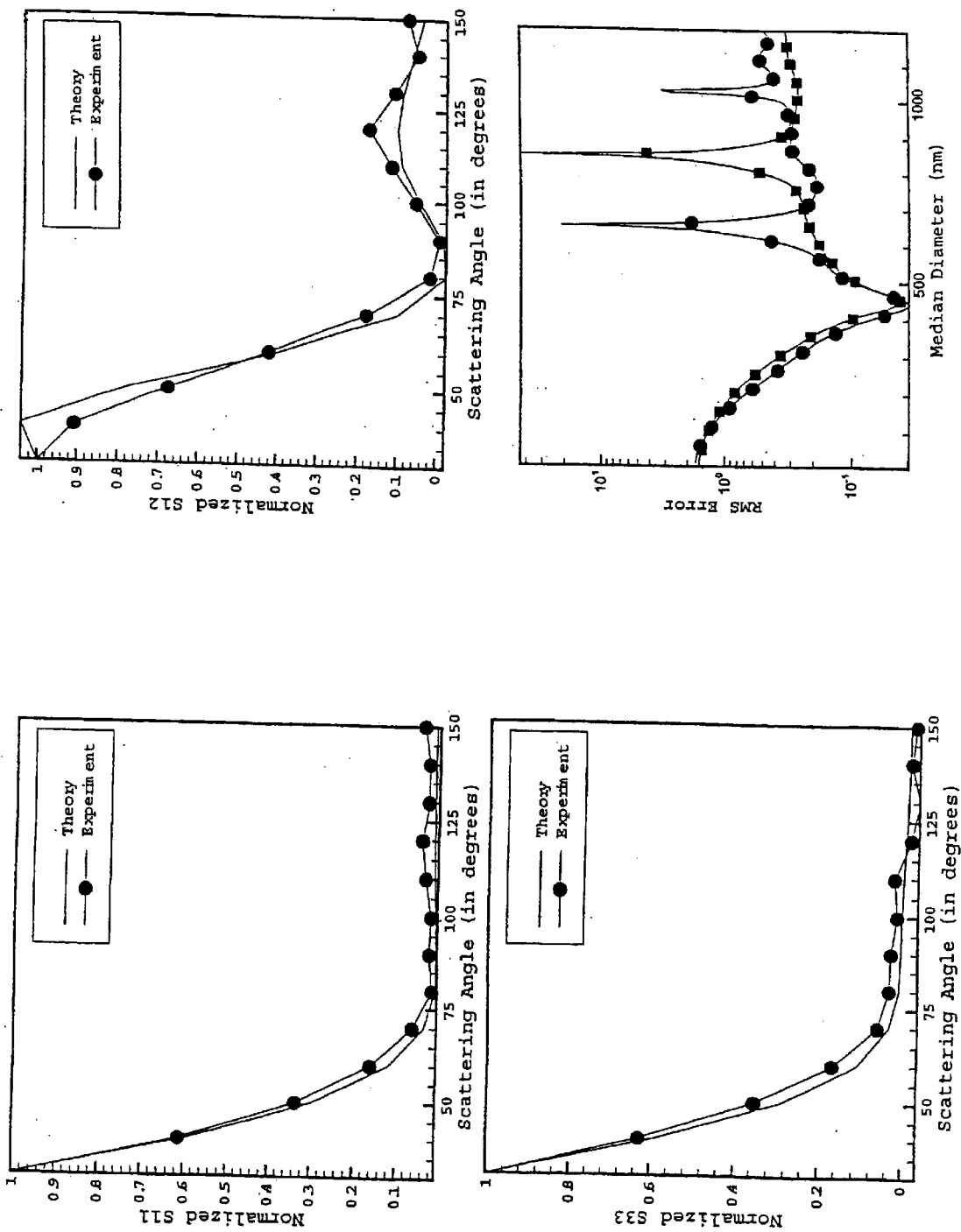
FIG. 10 is a graphical representation of the results of an experimental test utilizing latex spheres having an average diameter of 453 nm utilizing elliptically polarized radiation of two different wavelengths.

The results of the characterization process for the latex spheres having average diameters of 453 nm utilizing elliptically polarized radiation having a wavelength of 632 nm (red) are shown in FIG. 10. More specifically, the results shown in FIG. 10 include a graphical comparison of the theoretically predicted normalized $S_{ij}$ data for $S_{11}$, $S_{12}$, and $S_{33}$, and the experimentally determined normalized $S_{ij}$ data for $S_{11}$, $S_{12}$, and $S_{33}$. As can be seen in the graphical representations the experimental and theoretical $S_{ij}$ are generally in agreement. FIG. 10 further displays a graphical representation of the root-mean-square error for indicating a median diameter of approximately 453 nm.

Figure 11:
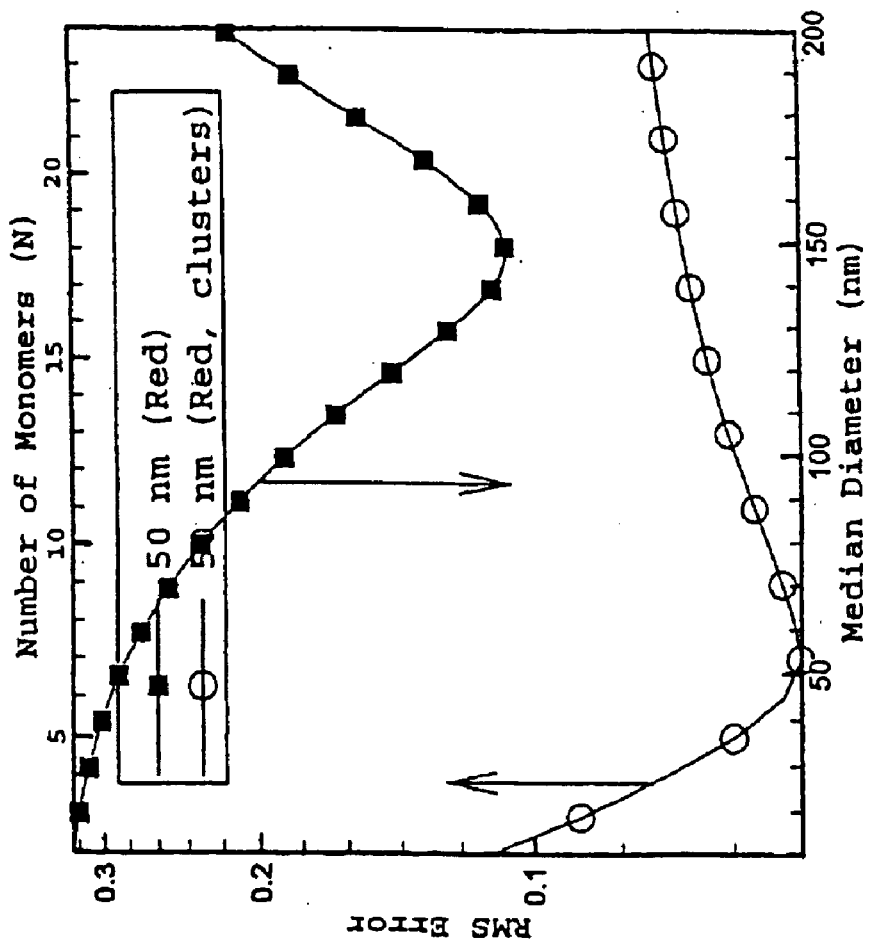
FIG. 11 is a graphical representation of the root-mean-square error for experiments performed with latex spheres having an average diameter of 50 nm particles indicating an experimentally predicted particle size of 150 nm suggesting the coagulation of some of the latex particles to form larger agglomerates.

FIG. 11 further displays the root-mean-square error for experiments performed with 50 nm latex particles. The results show an experimentally predicted particle size of 150 nm shown by the curve with squared symbols which is a significant difference from the 50 nm particles used. Since very small latex spheres tend to agglomerate into small clusters, the $S_{ij}$ experimental data was compared to the theoretical scattering for agglomerates of different median N. Each median N represents a log-normal distribution for the number of monomers forming the cluster. Note that the monomer diameter used in the calculations is 50 nm. The results indicated by the curve having circular symbols yields a very good match for small agglomerates with a median N of 7, suggesting that in that particular experiment about seven (7) latex monomers coagulated to form larger particles. Without having such a detailed analysis, no prior art characterization system could have determined this agglomeration.

Based on these results the following observations were made: (1) the available light scattering instruments would incorrectly indicate particles of 50 nm size; (2) traditional light scattering cannot distinguish agglomerates from spheres; (3) traditional light scattering cannot characterize the agglomerate size including the number of agglomerates; and (4) traditional light scattering will not correctly determine the mean monomer size of agglomerates.

Figure 12:
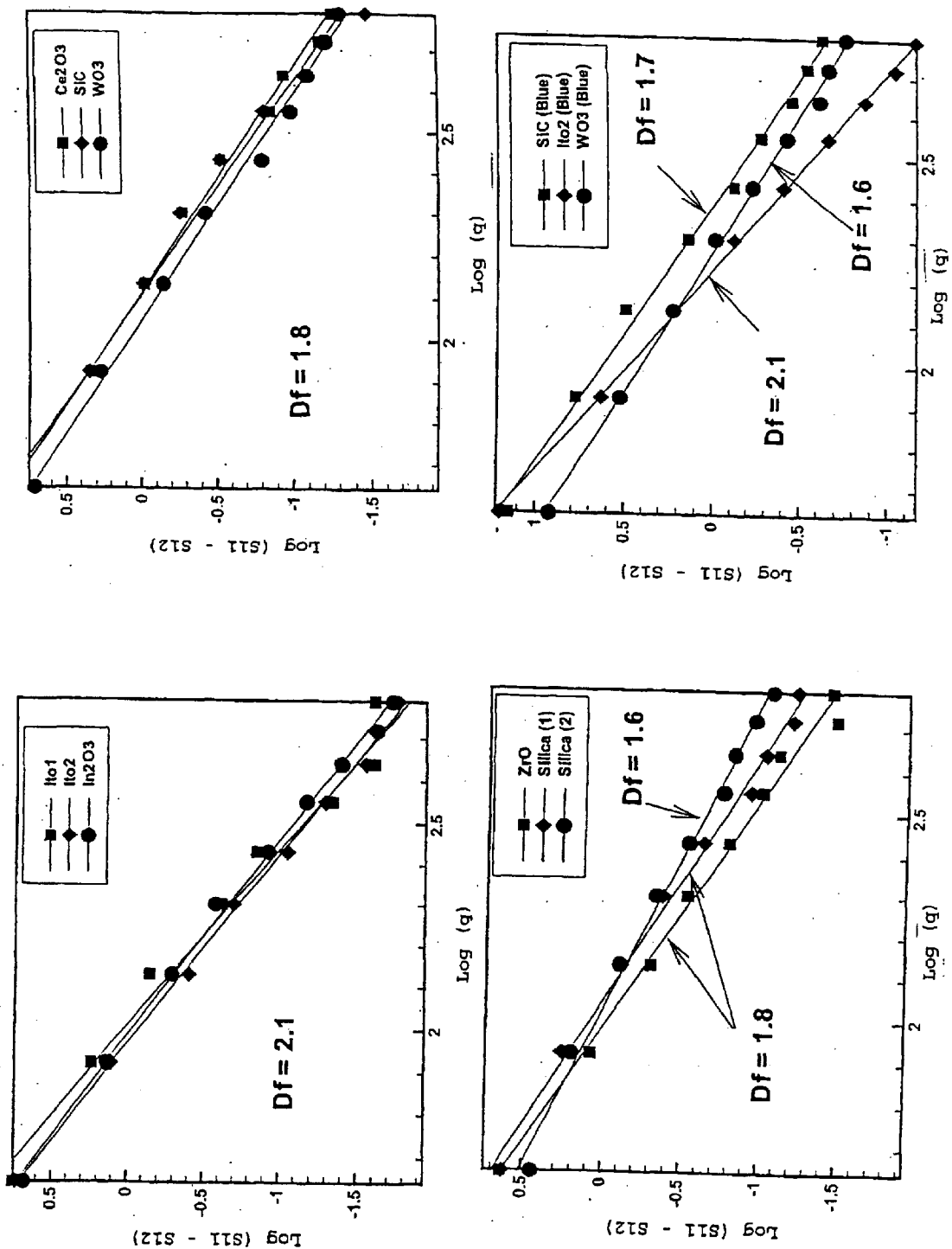
FIG. 12 is a graphical representation of a log-log plot of $S_{11}$–$S_{12}$ versus q indicating a fractal-like nature of the agglomerates.

In a second experiment using non-spherical particles, a series of measurements were made with different ceramic powders. The ceramic powders are agglomerates of small spheres each having diameters between 12 and 50 nm. Agglomerates of particles are typically characterized by the fractal dimension ($D_f$) and a number of primary spheres (N) that form the agglomerate. Since the number of primary spheres N itself can be a variable for a cloud of particles, a log-normal distribution was assumed for N. The experimental data points shown in log-log plots of $S_{11}$–$S_{12}$ versus q in FIG. 12 are fall along essentially straight lines indicating the fractal-like nature of the agglomerates being characterized. The slopes of the curves correspond to the fractal dimension $D_f$ as shown in the plots.

The experimental findings for each of the ceramic powder samples tested are shown below in Table 3 where N is the median number monomers, $D_f$ is the fractal dimension, dp is the monomer diameter, and Sigma is the standard deviation for N distribution.

TABLE 3

Number of Primary Spheres (N) and fractal Dimension $D_f$ for Ceramic Powders

| Material | N | $D_f$ | dp | Sigma |
|---|---|---|---|---|
| Silica | 300 | 1.6 | 12 | 1.12 |
| Zironium Oxide | 130 | 1.8 | 50 | 1.13 |
| Tungsten Oxide | 85 | 1.8 | 50 | 1.12 |
| Indium-Tin-Oxide | 460 | 2.1 | 20 | 1.14 |
| Silicon Carbide | 225 | 1.8 | 12 | 1.12 |
| Cerium Oxide | 400 | 1.8 | 20 | 1.14 |
| Indium Oxide | 625 | 2.1 | 12 | 1.12 |

The foregoing description of the preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

What is claimed is:

1. A non-intrusive method of characterizing particles through inverse analysis of experimental data based on measurements using elliptically polarized radiation comprising the steps of:

compiling a database of theoretical absorption and scattering data sets for particles;

determining optimum settings for an experimental test to rather an experimental absorption and scattering data set;

conducting the experimental test to obtain the experimental absorption and scattering data set; and comparing the experimental absorption and scattering data set to the theoretical absorption and scattering data sets of the database in order to determine an absorption and scattering data set which differs the least from the experimental absorption and scattering data set, wherein the step of compiling a database of theoretical absorption and scattering data sets for particles includes calculating an interaction of a theoretical incident planar wave having a wavelength ($\lambda$) on each monomer of an agglomerate having a diameter (d) and a complex index of refraction (m=n−ik) and interactions of portions of the theoretical incident planar wave scattered by each remaining monomer of the agglomerate using Maxwell's equations, and summing the calculated interactions for each monomer of said agglomerate.

2. The method of characterizing particles set forth in claim 1, further comprising the step of determining a distribution of the theoretical incident planar wave scattered by said agglomerate and an absorption of the theoretical incident planar wave by said agglomerate; and determining scattering matrix elements for said agglomerate based on the determined distribution of the theoretical incident planar wave scattered by said agglomerate and the determined absorption of the theoretical incident planar wave by said agglomerate.

3. The method of characterizing particles set forth in claim 2, further comprising the step of repeating the steps of calculating an interaction of a theoretical incident planar wave and interactions of portions of the theoretical incident planar wave, summing the calculated interactions, determining a distribution of the theoretical incident planar wave scattered by said agglomerate and an absorption of the theoretical incident planar wave by said agglomerate, and determining scattering matrix elements for said agglomerate for at least one possible combination of the wavelength ($\lambda$), the diameter (d), the complex index of refraction (n), and the absorption index (k).

4. The method of characterizing particles set forth in claim 2, wherein said particle is a fractal agglomerate having a fractal dimension $D_f$ and a prefactor $K_f$.

5. The method of characterizing particles set forth in claim 4, further comprising the step of repeating the steps of calculating an interaction of a theoretical incident planar wave and interactions of portions of the theoretical incident planar wave, summing the calculated interactions, determining a distribution of the theoretical incident planar wave scattered by said fractal agglomerate and an absorption of the theoretical incident planar wave by said fractal agglomerate, and determining scattering matrix elements for said fractal agglomerate for at least one possible combination of the wavelength ($\lambda$), the diameter (d), the complex index of refraction (n), the absorption index (k), the fractal dimension ($D_f$), and the prefactor ($K_f$).

6. A non-intrusive method of characterizing particles through inverse analysis of experimental data based on measurements using elliptically polarized radiation comprising the steps of:

compiling a database of theoretical absorption and scattering data sets for particles;

determining optimum settings for an experimental test to gather an experimental absorption and scattering data set;

conducting the experimental test to obtain the experimental absorption and scattering data set; and comparing the experimental absorption and scattering data set to the theoretical absorption and scattering data sets of the database in order to determine an absorption and scattering data set which differs the least from the experimental absorption and scattering data set, wherein the step of determining optimum settings for the experimental test to gather the experimental absorption and scattering data set includes estimating characteristics of the particles being characterized, and wherein the estimated characteristics of the particles being characterized includes data obtained utilizing a device selected from the group of a transmission electron microscope, a scanning electron microscope, and an atomic force microscope.

7. A non-intrusive method of characterizing particles through inverse analysis of experimental data based on measurements using elliptically polarized radiation comprising the steps of:

compiling a database of theoretical absorption and scattering data sets for particles;

determining optimum settings for an experimental test to gather an experimental absorption and scattering data set;

conducting the experimental test to obtain the experimental absorption and scattering data set; and comparing the experimental absorption and scattering data set to the theoretical absorption and scattering data sets of the database in order to determine an absorption and scattering data set which differs the least from the experimental absorption and scattering data set, wherein the step of determining optimum settings for the experimental test to gather the experimental absorption and scattering data set includes estimating characteristics of the particles being characterized, and wherein the step of determining optimum settings further includes selecting a wavelength of a theoretical elliptically polarized radiation based on said estimated characteristics of the particles being characterized, and selecting a theoretical set of polarizers and retarders each having an optical axis based on the selected wavelength.

8. The method of characterizing particles set forth in claim 7, wherein the step of determining optimum settings further includes selecting an orientation for the optical axis of one of said polarizers and retarders in said theoretical set, selecting an orientation for the optical axes of the remaining polarizers and retarders in said theoretical set, and determining an intensity of the theoretical elliptically polarized radiation scattered by the particle or agglomerate being characterized at a detection plane at at least one scattering angle.

9. The method of characterizing particles set forth in claim 8, wherein the steps of selecting an orientation for the optical axes of the remaining polarizers and retarders in said theoretical set and determining intensities of the theoretical elliptically polarized radiation scattered by the particle or agglomerate being characterized at a detection plane at at least one scattering angle are systematically repeated for each selected orientation.

10. The method of characterizing particles set forth in claim 9, wherein the step of determining optimum settings further includes selecting at least two orientations for the optical axes of said polarizers and retarders in said theoretical set which provide a high signal-to-noise ratio for use in the experimental test, wherein the high signal-to-noise ratio is determined in part by the determined intensities of the theoretical elliptically polarized radiation scattered by the particle or agglomerate being characterized.

11. A non-intrusive method of characterizing particles through inverse analysis of experimental data based on measurements using elliptically polarized radiation comprising the steps of:

compiling a database of theoretical absorption and scattering data sets for particles;

determining optimum settings for an experimental test to gather an experimental absorption and scattering data set;

conducting the experimental test to obtain the experimental absorption and scattering data set; and comparing the experimental absorption and scattering data set to the theoretical absorption and scattering data sets of the database in order to determine an absorption and scattering data set which differs the least from the experimental absorption and scattering data set, wherein the step of determining optimum settings for the experimental test to gather the experimental absorption and scattering data set includes estimating characteristics of the particles being characterized, and wherein the step of determining optimum settings further includes selecting a wavelength of an elliptically polarized radiation based on said estimated characteristics of the particles being characterized, and selecting a set of polarizers and retarders each having an optical axis based on the selected wavelength.

12. The method of characterizing particles set forth in claim 11, wherein the step of determining optimum settings further includes selecting an orientation for the optical axes of said polarizers and retarders in said set; and conducting a preliminary experimental test.

13. The method of characterizing particles set forth in claim 12, wherein the step of conducting a preliminary experimental test includes directing elliptically polarized radiation having the selected wavelength toward the particles to be characterized, modulating the polarization of the radiation before and after the radiation is incident on the particles, detecting radiation scattered by the particles to be characterized at at least one scattering angle, and repeating the steps of directing, modulating, and detecting at least four times;

wherein each successive repetition of the directing, modulating, and detecting steps follows a step of adjusting the orientation of the optical axes of said polarizers and retarders in said set.

14. The method of characterizing particles set forth in claim 13, wherein the step of modulating the polarization of the radiation before and after the radiation is incident on the particles includes utilizing at least one of said polarizers and retarders in said set before the radiation is incident on the particles and at least a second of said polarizers and retarders in said set after the radiation is incident on the particles; and wherein at least one detector is utilized to detect said radiation scattered by the particles to be characterized at at least one scattering angle and generate an output based on said detected radiation.

15. The method of characterizing particles set forth in claim 14, wherein the step of determining optimum settings further includes solving at least four equations simultaneously representing the outputs of said at least one detector in order to determine a preliminary experimental absorption and scattering data set.

16. The method of characterizing particles set forth in claim 14, wherein the step of determining optimum settings further includes comparing the preliminary experimental data set to the theoretical absorption and scattering data sets of the database in order to determine an absorption and scattering data set which differs the least from the preliminary experimental absorption and scattering data set; and replacing the estimated characteristics of the particles being characterized with new characteristics corresponding to the preliminary experimental absorption and scattering data set.

17. The method of characterizing particles set forth in claim 16, wherein the step of determining optimum settings further includes repeating the steps of conducting a preliminary experimental test, comparing the preliminary experimental absorption and scattering data set to the theoretical absorption and scattering data sets, and replacing the estimated characteristics of the particles being characterized with new characteristics corresponding to the preliminary experimental absorption and scattering data set at least one time.

18. A non-intrusive method of characterizing particles through inverse analysis of experimental data based on measurements using elliptically polarized radiation comprising the steps of:

compiling a database of theoretical absorption and scattering data sets for particles;

determining optimum settings for an experimental test to gather an experimental absorption and scattering data set;

conducting the experimental test to obtain the experimental absorption and scattering data set; and comparing the experimental absorption and scattering data set to the theoretical absorption and scattering data sets of the database in order to determine an absorption and scattering data set which differs the least from the experimental absorption and scattering data set, wherein the step of conducting the experimental test includes directing elliptically polarized radiation having a selected wavelength toward the particles to be characterized, modulating the polarization of the radiation before and after the radiation is incident on the particles to be characterized, detecting radiation scattered by the particles to be characterized at at least one scattering angle, and repeating the steps of directing, modulating, and detecting the elliptically polarized radiation at least one time.

19. The method of characterizing particles set forth in claim 18, wherein the step of modulating the polarization of the radiation before and after the radiation is incident on the particles to be characterized includes utilizing a first polarizer and a first retarder before the radiation is incident on the particles and a second polarizer and a second retarder after the radiation is incident on the particles; and wherein at least one detector is utilized to detect the radiation scattered by the particles to be characterized at the at least one scattering angle and generate an output based on the detected radiation.

20. The method of characterizing particles set forth in claim 19, wherein said first and second polarizers and retarders each have an optical axis; and wherein the step of conducting the experimental test includes establishing said axes at a first predetermined orientation.

21. The method of characterizing particles set forth in claim 20, wherein each successive repetition of the directing, modulating, and detecting steps follows a step of adjusting the orientation of the optical axis at least one of said first and second polarizers and retarders to a second predetermined orientation.

22. The method of characterizing particles set forth in claim 21, wherein the step of conducting the experimental test further includes solving at least four linear equations representing said detected elliptically polarized radiation in order to determine the experimental absorption and scattering data set.

23. The method of characterizing particles set forth in claim 22 further comprising the step of repeating the step of conducting an experimental test utilizing elliptically polarized radiation having a different wavelength at least once in order to limit the effects of particles having significant absorption properties at certain wavelengths.

24. The method of characterizing particles set forth in claim 23, further comprising the step of comparing the first experimental data set to the at least one subsequent data set in order to insure the integrity of the experimental data set to be compared to the theoretical absorption and scattering data sets of the database in order to determine an absorption and scattering data set which differs the least from the experimental absorption and scattering data set.

25. The method of characterizing particles set forth in claim 19, wherein the step of conducting the experimental test further includes correcting the output of said at least one detector.

26. The method of characterizing particles set forth in claim 25, wherein the step of correcting the output of said at least one detector includes multiplying the output by a corrective function, said corrective function selected to remove interface and multiple scattering effects which cause modulation of the elliptically polarized radiation.

27. The method of characterizing particles set forth in claim 26, wherein said first and second polarizers and retarders each have an optical axis;

wherein the step of conducting the experimental test includes establishing said axes at a first predetermined orientation;

wherein each successive repetition of the directing, modulating, and detecting steps follows a step of adjusting the orientation of the optical axis at least one of said first and second polarizers and retarders to a second predetermined orientation; and wherein the step of conducting the experimental test further includes solving at least four linear equations representing said detected elliptically polarized radiation in order to determine the experimental absorption and scattering data set.

28. A non-intrusive method of characterizing particles through inverse analysis of experimental data based on measurements using elliptically polarized radiation comprising the steps of:

compiling a database of theoretical absorption and scattering data sets for particles;

determining optimum settings for an experimental test to gather an experimental absorption and scattering data set;

conducting the experimental test to obtain the experimental absorption and scattering data set; and comparing the experimental absorption and scattering data set to the theoretical absorption and scattering data sets of the database in order to determine an absorption and scattering data set which differs the least from the experimental absorption and scattering data set, wherein the steps of conducting the experimental test to obtain the experimental absorption and scattering data set and comparing the experimental absorption and scattering data set to the theoretical absorption and scattering data sets of the database are repeated at least one time.

29. A non-intrusive method of characterizing particles through inverse analysis of experimental data obtained through measurements made using elliptically polarized radiation having a selected wavelength and based on predetermined optimized settings determined utilizing the selected wavelength utilizing a database of theoretical absorption and scattering data sets for particles comprising the steps of:

conducting an experimental test utilizing the predetermined optimized settings to obtain an experimental absorption and scattering data set; and comparing the experimental absorption and scattering data set to the theoretical absorption and scattering data sets of the database in order to determine an absorption and scattering data set which differs the least from the experimental absorption and scattering data set, wherein the step of conducting the experimental test includes directing elliptically polarized radiation having the selected wavelength toward the particles to be characterized, modulating the polarization of the radiation before and after the radiation is incident on the particles to be characterized, detecting radiation scattered by the particles to be characterized at at least one scattering angle, and repeating the steps of directing, modulating, and detecting the elliptically polarized radiation at least one time.

30. The method of characterizing particles set forth in claim 29, wherein the step of modulating the polarization of the radiation before and after the radiation is incident on the particles to be characterized includes utilizing a first polarizer and a first retarder before the radiation is incident on the particles and a second polarizer and a second retarder after the radiation is incident on the particles; and wherein at least one detector is utilized to detect the radiation scattered by the particles to be characterized at the at least one scattering angle and generate an output based on the detected radiation.

31. The method of characterizing particles set forth in claim 30, wherein said first and second polarizers and retarders each have an optical axis; and wherein the step of conducting the experimental test includes establishing said axes at a first predetermined orientation.

32. The method of characterizing particles set forth in claim 31, wherein each successive repetition of the directing, modulating, and detecting steps follows a step of adjusting the orientation of the optical axis at least one of said first and second polarizers and retarders to a second predetermined orientation.

33. The method of characterizing particles set forth in claim 32, wherein the step of conducting the experimental test further includes solving at least four linear equations representing said detected elliptically polarized radiation in order to determine the experimental absorption and scattering data set.

34. The method of characterizing particles set forth in claim 32, further comprising the step of comparing the first experimental data set to the at least one subsequent data set in order to insure the integrity of the experimental data set to be compared to the theoretical absorption and scattering data sets of the database in order to determine an absorption and scattering data set which differs the least from the experimental absorption and scattering data set.

35. An apparatus for characterizing particles through inverse analysis of experimental data based on measurements using elliptically polarized radiation comprising:

a radiation source for generating elliptically polarized radiation having a wavelength ($\lambda$);

a plurality of polarizers and retarders each having an optical axis an orientation of at least one of the optical axes being adjustable for modulating the elliptically polarized radiation before and after the radiation is incident on the particles;

at least one detector for detecting radiation scattered by the particles and generating an output;

a controller for adjusting the orientation of the optical axis of at least one of said polarizers and retarders; and a processor for receiving the output from said at least one detector, generating an experimental absorption and scattering data set based on the output of said at least one detector, and comparing the experimental absorption and scattering data set to theoretical absorption and scattering data sets in order to determine an absorption and scattering data set which differs the least from the experimental absorption and scattering data set.

36. The apparatus for characterizing particles in claim 35, wherein said plurality of polarizers and retarders include a first polarizer and a first retarder for modulating the elliptically polarized radiation before the radiation is incident on the particles and a second polarizer and a second retarder for modulating portions of the elliptically polarized radiation scattered by the particles.

37. The apparatus for characterizing particles in claim 36, wherein said at least one detector detects the scattered radiation over a range of scattering angles.

38. The apparatus for characterizing particles in claim 36, wherein said detector includes at least one fiber optic cable for receiving portions of the scattered radiation and directing the scattered radiation portions to said at least one detector.

39. The apparatus for characterizing particles in claim 37, further comprising a rotary stage for supporting the particles and at least one of said first polarizer and retarder, said second polarizer and retarder, and said at least one detector;

a motor for moving said rotary stage; and
wherein said controller controls the movement of said motor.

40. The apparatus for characterizing particles in claim 35, wherein said processor generates the theoretical absorption and scattering data sets.

41. The apparatus for characterizing particles in claim 35, wherein said processor determines an orientation for said plurality of polarizers and retarders.

42. An apparatus for characterizing particles through inverse analysis of experimental data based on measurements using elliptically polarized radiation comprising:

a radiation source for generating elliptically polarized radiation having a wavelength ($\lambda$) and directing the elliptically polarized radiation toward the particles;

a plurality of polarizer and retarder pairs for modulating the elliptically polarized radiation before and after the radiation is incident on the particles;

at least one detector for detecting radiation scattered by the particles; and a processor for receiving the output from said at least one detector, generating an experimental absorption and scattering data set based on the output of said at least one detector, comparing the experimental absorption and scattering data set to theoretical absorption and scattering data sets in order to determine an absorption and scattering data set which differs the least from the experimental absorption and scattering data set.

43. The apparatus for characterizing particles in claim 42, further comprising a moveable platform on which said plurality of pairs are mounted; and a controller for selectively moving said plurality of pairs into a path of the elliptically polarized radiation.

44. The apparatus for characterizing particles in claim 43, wherein said plurality of polarizer and retarder pairs include a first polarizer and retarder pair for modulating the elliptically polarized radiation before the radiation is incident on the particles and a second polarizer and retarder pair for modulating portions of the elliptically polarized radiation scattered by the particles.

45. The apparatus for characterizing particles in claim 44, wherein said at least one detector detects the scattered radiation over a range of scattering angles.

46. The apparatus for characterizing particles in claim 44, wherein said detector includes at least one fiber optic cable for receiving portions of the scattered radiation and directing the scattered radiation portions to said at least one detector.

47. The apparatus for characterizing particles in claim 45, further comprising a rotary stage for supporting the particles and at least one of a plurality of prisms for directing the elliptically polarized radiation and said at least one detector;

a motor for moving said rotary stage; and
wherein said controller controls the movement of said motor.

48. The apparatus for characterizing particles in claim 42, wherein said processor generates the theoretical absorption and scattering data sets.

49. The apparatus for characterizing particles in claim 42, wherein said processor determines an orientation for said plurality of polarizers and retarders.

50. A method of compiling a database of theoretical absorption and scattering data sets for use in characterizing particles through inverse analysis of experimental data based on measurements using elliptically polarized radiation comprising the steps of:

calculating an interaction of a theoretical incident planar wave having a wavelength ($\lambda$) on each monomer of an agglomerate having a diameter (d) and a complex index of refraction (m=n−ik) and interactions of portions of the theoretical incident planar wave scattered by each remaining monomer of the agglomerate using Maxwell's equations; and summing the calculated interactions for each monomer of said agglomerate.

51. The method of compiling a database of theoretical absorption and scattering data sets set forth in claim 50, further comprising the step of determining a distribution of the theoretical incident planar wave scattered by said agglomerate and an absorption of the theoretical incident planar wave by said agglomerate; and determining scattering matrix elements for said agglomerate based on the determined distribution of the theoretical incident planar wave scattered by said agglomerate and the determined absorption of the theoretical incident planar wave by said agglomerate.

52. The method of compiling a database of theoretical absorption and scattering data sets set forth in claim 51, further comprising the step of repeating the steps of calculating an interaction of a theoretical incident planar wave and interactions of portions of the theoretical incident planar wave, summing the calculated interactions, determining a distribution of the theoretical incident planar wave scattered by said agglomerate and an absorption of the theoretical incident planar wave by said agglomerate, and determining scattering matrix elements for said agglomerate for at least one possible combination of the wavelength ($\lambda$), the diameter (d), the complex index of refraction (n), and the absorption index (k).

53. The method of compiling a database of theoretical absorption and scattering data sets set forth in claim 51, wherein said particle is a fractal agglomerate having a fractal dimension $D_f$ and a prefactor $K_f$.

54. The method of compiling a database of theoretical absorption and scattering data sets set forth in claim 53, further comprising the step of repeating the steps of calculating an interaction of a theoretical incident planar wave and interactions of portions of the theoretical incident planar wave, summing the calculated interactions, determining a distribution of the theoretical incident planar wave scattered by said fractal agglomerate and an absorption of the theoretical incident planar wave by said fractal agglomerate, and determining scattering matrix elements for said fractal agglomerate for at least one possible combination of the wavelength ($\lambda$), the diameter (d), the complex index of refraction (n), the absorption index (k), the fractal dimension ($D_f$), and the prefactor ($K_f$).

55. The method of characterizing particles set forth in claim 28, wherein the step of determining optimum settings for the experimental test to gather the experimental absorption and scattering data set includes estimating characteristics of the particles being characterized.

56. The method of characterizing particles set forth in claim 55, wherein the step of determining optimum settings includes selecting a wavelength of a theoretical elliptically polarized radiation based on said estimated characteristics of the particles being characterized; and selecting a theoretical set of polarizers and retarders each having an optical axis based on the selected wavelength.

57. The method of characterizing particles set forth in claim 28, wherein the step of determining optimum settings includes conducting a preliminary experimental test.

58. The method of characterizing particles set forth in claim 57, wherein the step of determining optimum settings further includes selecting a wavelength of an elliptically polarized radiation based on estimated characteristics of the particles being characterized; and selecting a set of polarizers and retarders each having an optical axis based on the selected wavelength.

59. The method of characterizing particles set forth in claim 58, wherein the step of conducting a preliminary experimental test includes directing elliptically polarized radiation having the selected wavelength toward the particles to be characterized, modulating the polarization of the radiation before and after the radiation is incident on the particles, detecting radiation scattered by the particles to be characterized at at least one scattering angle, and repeating the steps of directing, modulating, and detecting at least four times.

* * * * *

UNITED STATES PATENT AND TRADEMARK OFFICE
CERTIFICATE OF CORRECTION

PATENT NO. : 6,721,051 B2
APPLICATION NO. : 09/956388
DATED : April 3, 2004
INVENTOR(S) : Mengüc et al.

It is certified that error appears in the above-identified patent and that said Letters Patent is hereby corrected as shown below:

On the title page: Item [12] should read --Mengüc et al--.

Column 19, line 9, please replace " rather" with --gather--.

Signed and Sealed this

Tenth Day of October, 2006

JON W. DUDAS
*Director of the United States Patent and Trademark Office*

UNITED STATES PATENT AND TRADEMARK OFFICE
CERTIFICATE OF CORRECTION

PATENT NO. : 6,721,051 B2  Page 1 of 1
APPLICATION NO. : 09/956388
DATED : April 13, 2004
INVENTOR(S) : Mengüc et al.

It is certified that error appears in the above-identified patent and that said Letters Patent is hereby corrected as shown below:

On the title page: Item [12] should read --Mengüc et al--.

Column 19, line 9, please replace " rather" with --gather--.

This certificate supersedes Certificate of Correction issued October 10, 2006.

Signed and Sealed this

Fourteenth Day of November, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,721,051 B2 | Page 1 of 1 |
| APPLICATION NO. | : 09/956388 | |
| DATED | : April 13, 2004 | |
| INVENTOR(S) | : Mengüç, et al. | |

It is certified that error appears in the above-identified patent and that said Letters Patent is hereby corrected as shown below:

On the title page: Item [12] should read -- Mengüç, et al.--.

Column 19, line 9, please replace "rather" with --gather--.

This certificate supersedes Certificate of Correction issued October 10, 2006 and November 14, 2006.

Signed and Sealed this

Nineteenth Day of December, 2006

JON W. DUDAS
*Director of the United States Patent and Trademark Office*